(12) United States Patent
Lee et al.

(10) Patent No.: US 10,055,837 B2
(45) Date of Patent: Aug. 21, 2018

(54) METHOD OF AND APPARATUS FOR MEASURING BIOMETRIC INFORMATION

(71) Applicant: SAMSUNG ELECTRONICS CO., LTD., Suwon-si (KR)

(72) Inventors: Jeong-gun Lee, Seoul (KR); Seong-je Cho, Suwon-si (KR); Kwang-bok Kim, Incheon (KR); Chul-ho Cho, Seongnam-si (KR)

(73) Assignee: SAMSUNG ELECTRONICS CO., LTD., Suwon (KR)

( * ) Notice: Subject to any disclaimer, the term of this patent is extended or adjusted under 35 U.S.C. 154(b) by 62 days.

(21) Appl. No.: 14/932,294

(22) Filed: Nov. 4, 2015

(65) Prior Publication Data

US 2016/0125600 A1    May 5, 2016

(30) Foreign Application Priority Data

Nov. 4, 2014   (KR) .................. 10-2014-0152083
Nov. 3, 2015   (KR) .................. 10-2015-0153983

(51) Int. Cl.
| G06K 9/00 | (2006.01) |
| G06T 7/00 | (2017.01) |
| G06K 9/62 | (2006.01) |
| G06K 9/46 | (2006.01) |
| G06F 19/10 | (2011.01) |
| G01N 21/84 | (2006.01) |
| G06T 7/90 | (2017.01) |

(52) U.S. Cl.
CPC ....... *G06T 7/0012* (2013.01); *G01N 21/8483* (2013.01); *G06F 19/10* (2013.01); *G06K 9/4652* (2013.01); *G06K 9/4661* (2013.01); *G06K 9/6201* (2013.01); *G06T 7/90* (2017.01); *G06K 2009/4666* (2013.01)

(58) Field of Classification Search
None
See application file for complete search history.

(56) References Cited

U.S. PATENT DOCUMENTS

| 3,932,133 A | 1/1976 | Ishikawa |
| 5,236,848 A | 8/1993 | Bitsch |

(Continued)

FOREIGN PATENT DOCUMENTS

| CN | 1151525 A | 6/1997 |
| CN | 1653330 A | 8/2005 |

(Continued)

OTHER PUBLICATIONS

Communication dated Oct. 24, 2016 issued by the Taiwan Intellectual Property Office in counterpart Taiwanese Patent Application No. 104136250.

(Continued)

*Primary Examiner* — Vikkram Bali
(74) *Attorney, Agent, or Firm* — Sughrue Mion, PLLC

(57) ABSTRACT

A method of and an apparatus for measuring biometric information are provided. The method includes receiving an image of a biosensor including a reagent pad on which a sample is collected, and comparing brightness information of a reacting region of the reagent pad in the received image with reference brightness information in the received image to determine a value of a reagent reaction between the reagent pad and the sample.

27 Claims, 42 Drawing Sheets

(56) References Cited

U.S. PATENT DOCUMENTS

| | | | |
|---|---|---|---|
| 5,837,546 A | | 11/1998 | Allen et al. |
| 6,586,257 B1 | | 7/2003 | Vuong |
| 7,267,799 B1 | | 9/2007 | Borich et al. |
| 7,534,393 B2 | | 5/2009 | Catt et al. |
| 7,538,336 B2 | | 5/2009 | Brock et al. |
| 7,659,086 B2 | | 2/2010 | Harris et al. |
| 7,803,322 B2 | | 9/2010 | Borich et al. |
| 8,630,867 B2 | | 1/2014 | Yoo |
| 9,063,091 B2 | * | 6/2015 | Tsai .................. G01N 21/78 |
| 2003/0049849 A1 | | 3/2003 | Mori et al. |
| 2012/0063652 A1 | * | 3/2012 | Chen .................. G01N 21/274 |
| | | | 382/128 |
| 2012/0179383 A1 | | 7/2012 | Yeo et al. |
| 2012/0189509 A1 | * | 7/2012 | Hsiao ................ G01N 21/8483 |
| | | | 422/400 |
| 2012/0244624 A1 | * | 9/2012 | Hsiao ................ G01N 21/8483 |
| | | | 436/86 |
| 2013/0070805 A1 | * | 3/2013 | Coln .................. G01K 7/186 |
| | | | 374/1 |
| 2013/0112557 A1 | * | 5/2013 | Javitt ................ A61B 5/14532 |
| | | | 204/403.01 |
| 2013/0118920 A1 | | 5/2013 | Craggs et al. |
| 2013/0267032 A1 | | 10/2013 | Tsai et al. |
| 2014/0027308 A1 | * | 1/2014 | Harrison ............ A61B 5/14532 |
| | | | 205/777.5 |
| 2014/0051173 A1 | * | 2/2014 | Barstis ................ G01N 21/78 |
| | | | 436/43 |
| 2014/0072189 A1 | * | 3/2014 | Jena ................ G01N 21/8483 |
| | | | 382/128 |
| 2016/0124206 A1 | * | 5/2016 | Bose .................. G02B 21/365 |
| | | | 348/79 |

FOREIGN PATENT DOCUMENTS

| | | |
|---|---|---|
| CN | 1727898 A | 2/2006 |
| CN | 1776407 A | 5/2006 |
| CN | 102954962 A | 3/2013 |
| EP | 0953149 B1 | 9/2004 |
| JP | 2003-121260 A | 4/2003 |
| KR | 10-0251999 B1 | 6/2000 |
| KR | 10-0384795 B1 | 5/2003 |
| KR | 10-2008-0009396 A | 1/2008 |
| KR | 10-2010-0014065 A | 2/2010 |
| KR | 10-1092351 B1 | 12/2011 |
| KR | 10-2013-0012744 A | 2/2013 |
| KR | 10-2013-0092571 A | 8/2013 |
| KR | 10-2013-0142564 A | 12/2013 |
| KR | 20-0470398 Y1 | 12/2013 |
| KR | 10-2014-0045802 A | 4/2014 |
| WO | 2013/116831 A1 | 8/2013 |
| WO | 2013/149598 A1 | 10/2013 |
| WO | 2014/113770 A1 | 7/2014 |

OTHER PUBLICATIONS

Search Report dated Jan. 29, 2016, issued by the International Searching Authority in counterpart International Patent Application No. PCT/KR2015/011815 (PCT/ISA/210).
Written Opinion dated Jan. 29, 2016, issued by the International Searching Authority in counterpart International Patent Application No. PCT/KR2015/011815 (PCT/ISA/237).
Communication dated Mar. 24, 2016, issued by the European Patent Office in counterpart European Patent Application No. 15192907.2.
Hong, et al.; "Development of the Smartphone-Based Colorimetry for Multi-Analyte Sensing Arrays", The Royal Society of Chemistry, Lab Chip, Feb. 2014, vol. 14, 8 pages total.
Ozcan: "Mobile Phones Democratize and Cultivate Next-Generation Imaging, Diagnostics and Measurement Tools", The Royal Society of Chemistry, Lab Chip, Feb. 2014, 8 pages total.
Shen, et al.; "Point-of-Care Colorimetric Detection with a Smartphone", The Royal Society of Chemistry, Lab Chip, Sep. 2012, vol. 12, 4 pages total.
Erickson, et al.; "Smartphone Technology Can be Transformative to the Deployment of Lab-On-Chip Diagnostics", The Royal Society of Chemistry, Lab Chip, Mar. 2014, 6 pages total.
Communication dated Aug. 17, 2015, issued by the Korean Intellectual Property Office in counterpart Korean Application No. 10-2014-0152083.
Communication dated Oct. 31, 2017, issued by the State Intellectual Property Office of the People's Republic of China in counterpart Chinese Patent Application No. 201510742655.0.
Communication dated Jun. 20, 2018, issued by the State Intellectual Property Office of the People's Republic of China in counterpart Chinese Patent Application No. 201510742655.0.

* cited by examiner (a)

(b)

Detector

Biosensor (a)　　　　　　　(b)　　　　　　　(c)

PN106450KR GILDONG HONG

METHOD OF AND APPARATUS FOR MEASURING BIOMETRIC INFORMATION

CROSS-REFERENCE TO RELATED APPLICATION

This application claims priority from Korean Patent Application No. 10-2014-0152083, filed on Nov. 4, 2014, in the Korean Intellectual Property Office, and Korean Patent Application No. 10-2015-0153983, filed on Nov. 3, 2015, in the Korean Intellectual Property Office, the disclosure of which is incorporated herein in its entirety by reference.

BACKGROUND

1. Field

Methods and apparatuses consistent with exemplary embodiments relate to measuring biometric information from a collected sample.

2. Description of the Related Art

Methods of measuring biometric information from a sample collected from a body have been continuously developed. Urine or blood may be collected to be used as a sample, however, with the constant development of such methods, a method of measuring biometric information regarding, for example, diabetes from a sweat or tear sample has been developed. Also, a method of measuring biometric information from a sample collected from saliva or an exhaled breath has been developed.

According to a method of measuring biometric information from a sample, biometric information may be measured via a qualitative analysis of determining a positive or a negative reaction by checking with the naked eye a reaction result of urine with respect to a reagent on a urine diagnostic strip.

With regard to measuring biometric information, many reagent reactions are used for diagnosing various diseases. In addition, not only a qualitative analysis of a positive/negative reaction, but also a quantitative analysis of determining a disease status via a measured numerical value is used.

Various types of information, such as a diabetes level, an acid level (pH), and a protein level, may be obtained via reaction tests using urine and/or blood, but measuring devices used in this regard are provided according to types of information to be measured. Also, the measuring devices have medium and large sizes, are expensive, and require specialized knowledge to be used, and thus are limited to use by experts, such as medics and medical technologists.

Accordingly, home or portable measuring devices that may be easily used by ordinary people have been actively developed, and methods of measuring biometric information by inputting sample information to a portable terminal, such as a smart phone, have been studied.

A technology of analyzing a strip on which a sample is collected through an optical image sensor, such as a camera, included in a terminal has been developed in detail. Also, to accurately analyze a reaction of the sample and a reagent pad attached to the strip, a method of obtaining an accurate discoloration level of the reagent pad by analyzing and calibrating the discoloration level has been actively studied.

However, calibration may not be accurately performed by using a method of comparing a discoloration value with standard color codes to calibrate the discoloration level of the reagent pad because a color may be differently displayed based on lighting of a place where the sample is measured. For example, when the sample is measured in a dark place or a shadow of a user accessing the terminal covers the strip, a camera sensor may wrongly recognize the discoloration value.

Also, when a temperature of a reagent is considerably different from room temperature where the measuring is performed, a quantitative value of a quantitative reaction according to the temperature may be calibrated. Also, when the reagent is sensitive to temperature, i.e., when the discoloration level largely varies with temperature, quantitative value calibration according to temperature is necessary.

Accordingly, calibrating methods for reducing various errors that may be generated under various measuring environments and methods of deriving accurate results by calibrating a quantitative value according to brightness in a reagent reaction are being developed.

SUMMARY

Exemplary embodiments address at least the above problems and/or disadvantages and other disadvantages not described above. Also, one or more exemplary embodiments are not required to overcome the disadvantages described above, and an exemplary embodiment may not overcome any of the problems described above.

According to an aspect of an exemplary embodiment, there is provided a method of measuring biometric information, the method being used by a terminal and including receiving an image of a biosensor including a reagent pad on which a sample is collected, and comparing brightness information of a reacting region of the reagent pad in the received image with reference brightness information in the received image to determine a value of a reagent reaction between the reagent pad and the sample.

The method may further include determining the brightness information of the reacting region of the reagent pad in the received image, and determining the reference brightness information in the received image.

The method may further include determining a result of the reagent reaction based on the determined value.

The method may further include identifying the biosensor based on identification (ID) information that is displayed on the biosensor in the received image, and determining a result of the reagent reaction based on information of the identified biosensor.

The ID information that is displayed in the received image may include at least one among a quick response code, a barcode, an image, and text.

The method may further include determining whether an expiration date of the biosensor has passed, the expiration date being included in the ID information, and displaying at least one among unserviceability of the biosensor and invalidity of the reagent reaction, in response to the determining that the expiration date has passed.

The method may further include determining a temperature of the sample based on temperature information that is indicated by a temperature measurer that is attached to the reagent pad in the received image.

The determining may include determining the value of the reagent reaction based on the determined temperature of the sample and temperature information of a reaction of the sample.

The temperature measurer may be configured to be attached to at least one among a sample inlet of the reagent pad and the reacting region of the reagent pad.

The method may further include determining whether the temperature of the sample is equal to or higher than a pre-set temperature, and displaying a message indicating impossibility of measuring the sample.

The method may further include determining whether the temperature of the sample is lower than or equal to a pre-set temperature, and displaying a message indicating impossibility of measuring the sample.

The temperature measurer may be displayed on the reagent pad in at least one among a linear shape, a radial shape, and a circular shape.

The method may further include measuring a room temperature, using a temperature sensor that is included in the terminal.

The method may further include determining a room temperature that is indicated by a temperature sensor that is attached to the biosensor in the received image.

The reference brightness information may indicate different discrete brightnesses with respect to a same color, and comparing the brightness information of the reacting region may include detecting a first brightness information among the reference brightness information, the first brightness information corresponding to the bright information of the reacting region, and determining the value of the reagent reaction corresponding to the first brightness information.

The reference brightness information may indicate different continuous brightnesses with respect to a same color, the different continuous brightnesses may be disposed continuously within the reference brightness information, and comparing the brightness information of the reacting region may include detecting a first brightness information among the reference brightness information, the first brightness information corresponding to the bright information of the reacting region, detecting a location in which the first brightness information is located within the reference brightness information, and determining the value of the reagent reaction corresponding to the detected location.

The reference brightness information may indicate different discrete brightnesses with respect to a same color, and comparing the brightness information of the reacting region may include detecting a region including pixels having same brightnesses as a brightness of a part corresponding to the reaction region in the image, recognizing a shape of the detected region, determining an actual brightness of the reaction region based on the recognized shape, and determining the value of the reagent reaction corresponding to the determined actual brightness.

The value of the reagent reaction may correspond to a color and a brightness of the sample in a database that is stored in a storage of the terminal.

The reagent pad may further include a control line having a color changing according to the reagent reaction.

The biosensor may include reagent pads supporting reagent reactions between the reagent pads and the sample.

The method may further include identifying the biosensor based on locations of the reagent pads in the received image.

The biosensor may be configured to analyze at least one among urine, blood, sweat, a tear, saliva, and an exhaled breath.

According to an aspect of another exemplary embodiment, there is provided a terminal for measuring biometric information, the terminal including an input interface configured to receive an image of a biosensor including a reagent pad on which a sample is collected, a storage configured to store the received image, and a controller configured to compare brightness information of a reacting region of the reagent pad in the received image with reference brightness information in the received image to determine a value of a reagent reaction between the reagent pad and the sample.

The controller may be further configured to determine the brightness information of the reacting region of the reagent pad in the received image, and determine the reference brightness information in the received image.

The controller may be further configured to determine a result of the reagent reaction based on the determined value.

According to an aspect of another exemplary embodiment, there is provided a biosensor for supporting measuring of biometric information, the biosensor including a reagent pad including a sample inlet configured to collect a sample, and a reacting region at which the collected sample reacts, an identification information display region configured to display ID information of the biosensor, and a reference brightness display region configured to display different brightness information with respect to a same color. The reacting region is configured to change a color according to a result of the reaction between the reacting region and the sample.

The sample inlet may include a temperature measurer configured to measure a temperature of the collected sample.

The biosensor may further include a reference color display region configured to display different color information with respect to the reacting region.

The reacting region may include dyes configured to change respective colors according to the result of the reaction between the reacting region and the sample.

According to an aspect of another exemplary embodiment, there is provided an apparatus for measuring biometric information, the apparatus including an input interface configured to capture an image of a reagent pad on which a sample is collected, the reagent pad including a region at which the sample reacts, and the reagent pad including reference brightnesses, and a controller configured to compare a brightness of the region in the captured image with the reference brightnesses in the captured image to determine a result of the reaction between the region and the sample.

The apparatus may further include a display configured to display the captured image and the result of the reaction between the region and the sample.

According to an aspect of another exemplary embodiment, there is provided a method of a terminal measuring biometric information, the method including capturing an image of a biosensor comprising a reagent pad on which a sample in collected, transmitting the image to a server, receiving the biometric information from the server, the biometric information being determined by comparing brightness information of a reaction region of the reagent pad in the image with reference brightness information in the image, and displaying the received biometric information.

BRIEF DESCRIPTION OF THE DRAWINGS

The above and/or other aspects will be more apparent by describing exemplary embodiments with reference to the accompanying drawings, in which.

DETAILED DESCRIPTION

Figure 1:
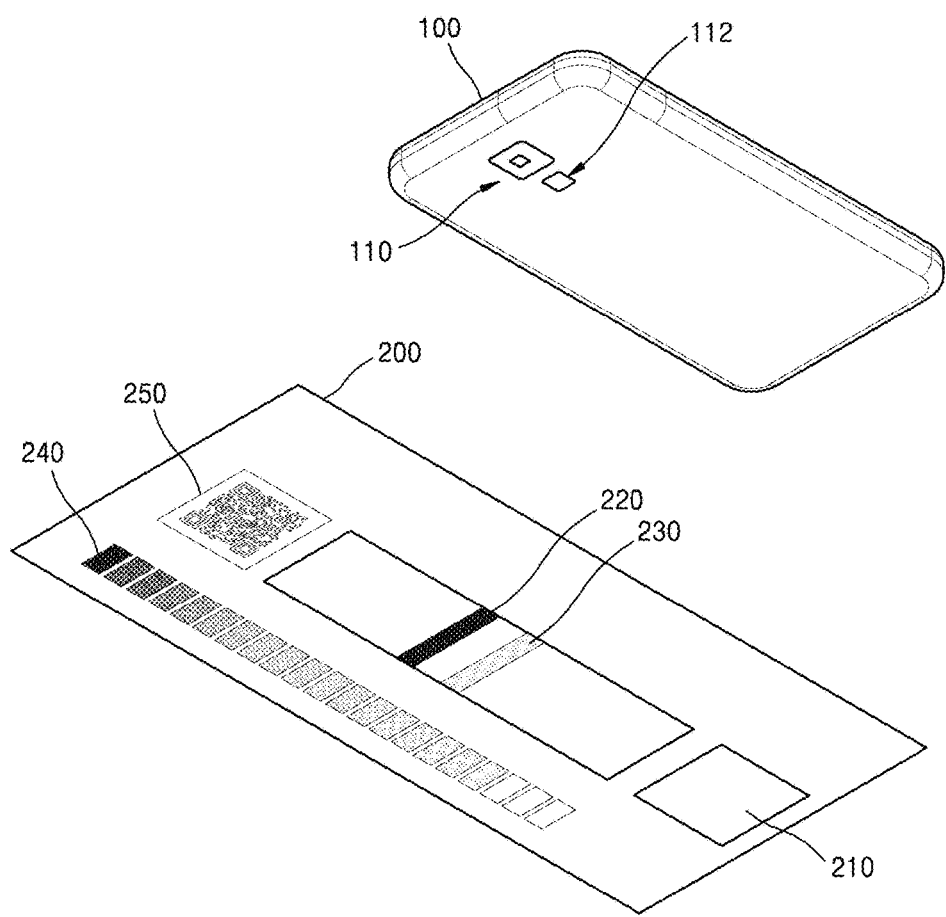
FIG. 1 is a perspective view illustrating a terminal and a biosensor, according to an exemplary embodiment.

Exemplary embodiments are described in greater detail with reference to the accompanying drawings.

Exemplary embodiments of the present disclosure may be diversely modified. Accordingly, exemplary embodiments are illustrated in the drawings and are described in detail in the detailed description. However, it is to be understood that the present disclosure is not limited to an exemplary embodiment, but includes all modifications, equivalents, and substitutions without departing from the scope and spirit of the present disclosure. Also, well-known functions or constructions may not be described in detail because they would obscure the disclosure with unnecessary detail.

In the following description, the same drawing reference numerals are used for the same elements even in different drawings. The matters defined in the description, such as detailed construction and elements, are provided to assist in a comprehensive understanding of the exemplary embodiments. Thus, it is apparent that the exemplary embodiments can be carried out without those specifically defined matters.

As used herein, the term "and/or" includes any and all combinations of one or more of the associated listed items. Expressions such as "at least one of," when preceding a list of elements, modify the entire list of elements and do not modify the individual elements of the list.

Hereinafter, a method of obtaining and processing, by a terminal, biometric information from a biosensor that collected a sample including the biometric information, according to one or more exemplary embodiments, will be described in detail.

FIG. 1 is a perspective view illustrating a terminal 100 and a biosensor 200, according to an exemplary embodiment.

The terminal 100 according to an exemplary embodiment includes an input interface 110. The input interface 110 may be an input interface including a module that may be manipulated by a user and also allow an image, voice, text of the user to be input from the terminal 100, such as a button input interface when the terminal 100 includes a button or an optical input interface when the terminal 100 includes an optical image sensor. In FIG. 1, the terminal 100 includes, on a rear surface, a camera receiving an optical image, and includes, below the camera, a non-contact temperature sensor 112. Because the non-contact temperature sensor 112 is also used to input an external temperature into the terminal 100, the non-contact temperature sensor 112 may be understood to be the input interface 110 of the terminal 100.

The biosensor 200 is a device used to collect and analyze a sample including biometric information. Examples of the sample including the biometric information may include urine, blood, sweat, a tear, saliva, and an exhaled breath, and the biosensor 200 may be used to determine a condition of a body of the user as a reagent pad and the sample chemically or physically react with each other and the reagent pad is discolored or displays information.

Technologies of measuring various types of biometric information through an exhaled breath are being developed. Because an exhaled breath of a person or an animal contains intrinsic characteristics, the exhaled breath may operate as a type of a chemical breathprint. Because the exhaled breath not only discharges carbon dioxide, but may also discharge a volatile organic compound, such as acetone, toluene, nitrogen monoxide, or ammonia, a disease, such as diabetes, may be diagnosed by measuring a discharge amount of each material in the exhaled breath. For example, because a normal person who does not have diabetes discharges an acetone gas of about 900 parts per billion (ppb) through an exhaled breath, and a patient who has diabetes discharges an acetone gas of about 1800 ppb through an exhaled breath, diabetes may be diagnosed by measuring a discharge amount of an acetone gas.

Various diseases, such as diabetes, asthma, lung cancer, nephropathy, and heart disease, may be diagnosed by using the biosensor 200, such as an exhaled breath sensor, and as well as diagnosing a disease, a sick house syndrome may be determined by measuring concentration of harmful substances, such as toluene and formaldehyde, found in a new building. Also, because acetone is mixed in an exhaled breath when fat is burnt, it may be determined whether a person running on a treadmill is having a sufficient diet effect.

An exhaled breath is measured by measuring a discharge amount of a substance therein, or alternatively, may be measured based on discoloration information as the substance in the exhaled breath changes a color of the biosensor 200 via a chemical or physical reaction (dye reaction) (for example, a color change according to pH in a bromothymol blue (BTB) solution). Accordingly, a sample collected from the exhaled breath may be measured by using the biosensor to measure biometric information, according to an exemplary embodiment.

The biosensor 200 according to an exemplary embodiment includes a sample inlet 210 into which a sample is input for a reaction with a reagent pad, and a control line 220 used as a criteria for paired-comparison of the reaction on the reagent pad. The biosensor 200 further includes a test line 230 for directly determining a reaction between a reagent of the reagent pad and the sample, reference brightness information display region 240 used as a comparison object for determining color and brightness levels in the test line 230, and an identification (ID) information display region 250 for identifying ID information of the biosensor 200.

According to FIG. 1, the reaction between the sample and the reagent pad according to an exemplary embodiment enables a user of the terminal 100 to perform a qualitative analysis based on a reaction result according to discoloration of the control line 220 and the test line 230 and also a qualitative analysis based on a discoloration level or a brightness change. For example, in a pregnancy test, pregnancy may be determined based on discoloration of a control line and a test line.

As shown in FIG. 1, the biosensor 200 according to an exemplary embodiment includes the sample inlet 210 into which the sample is input for the reaction between the sample and the reagent pad, wherein the sample input into the sample inlet 210 may react with the control line 220 and the test line 230 of the reagent pad according to an immunochromatography method.

The immunochromatography method uses a reaction characteristic of an antibody and an antigen, wherein the antibody is a type of protein made in a body to remove a pathogen entering the body, and the antigen is a material like a pathogen that the antibody combines with. One type of antibody combines with a part of an antigen. For example, when immunochromatography is applied to a pregnancy test, human chorionic gonadotropin (HCG) discharged from blood or urine after pregnancy is used as the antigen to prepare two types of antibodies that combine with HCG. The antibodies of one type are attached to gold particles in reddish purple, and the antibodies of the other type are fixed on a thin plate of nitrocellulose membrane in a linear shape. Because the antibodies are invisible protein, no color is shown in a test line fixed on the nitrocellulose membrane.

When urine is dropped on the HCG, the antibodies fixed to the gold particles combine with the HCG and pass through the nitrocellulose membrane by capillarity action. When the antibodies combined with the HCG pass the test line, the antibodies combined with the HCG combine with the antibodies fixed to the nitrocellulose membrane, and thus the gold particles form a reddish purple linear shape, thereby determining pregnancy by determining such discoloration with naked eyes. When the HCG is not contained in urine, the HCG is not combined with the antibodies in the test line, and no line is shown, and thus a user may determine nonpregnancy.

Meanwhile, a test finish line (may also be referred to as a "control line" herein), which is always shown regardless of pregnancy, is a line designed to be shown all the time regardless of existence of the HCG. The test finish line is also a line using a reaction between antigens and antibodies, and displays to the user information that a strip function us is normal and information that the user may determine a result because a test is finished.

Hereinabove, the immunochromatography method is applied to the pregnancy test, but it would be obvious to one of ordinary skill in the art that the immunochromatography may also be used to diagnose ovulation, hepatitis, AIDS, or the like.

Figure 2:
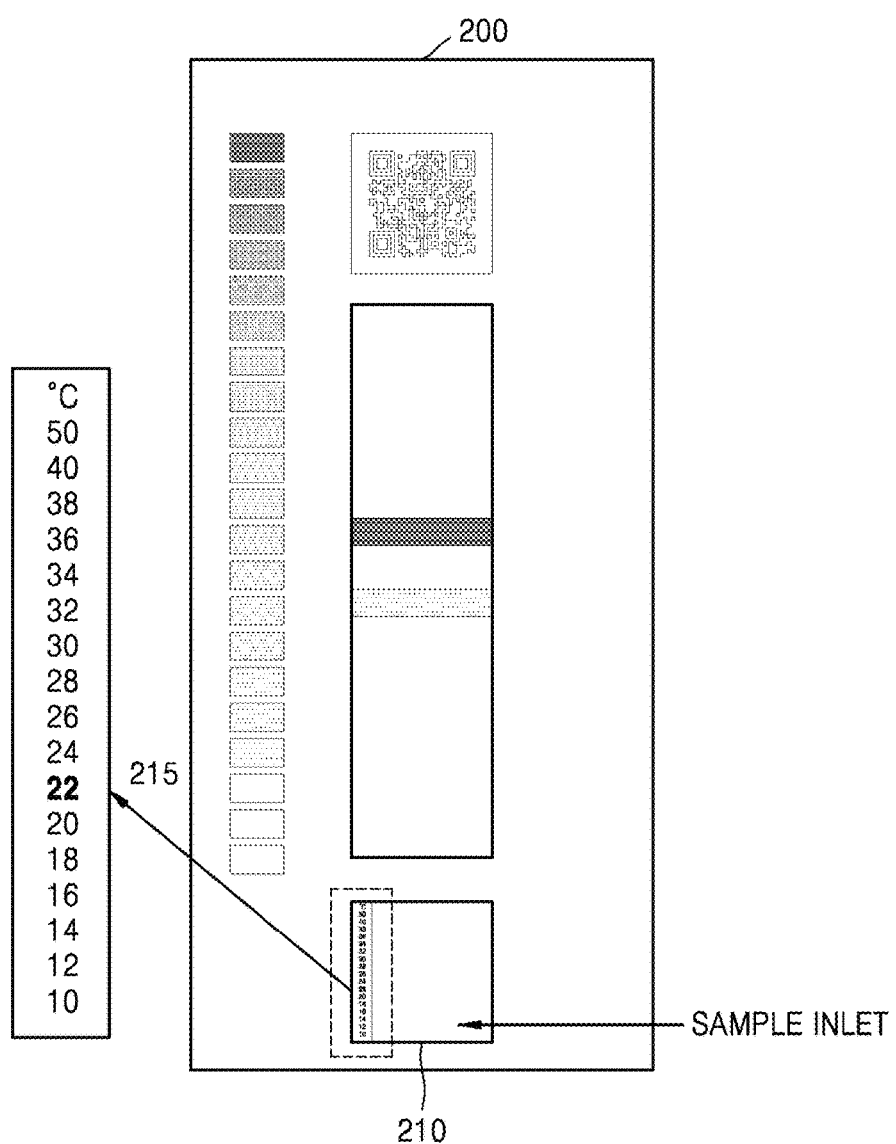
FIG. 2 is a view illustrating a reagent pad to which a temperature measurer is attached, according to an exemplary embodiment.

FIG. 2 is a view illustrating a reagent pad to which a temperature measurer 215 is attached, according to an exemplary embodiment.

The biosensor 200 according to an exemplary embodiment includes the temperature measurer 215 at the sample inlet 210. Because a temperature of a sample may function as a variable while measuring biometric information, the temperature of the sample may be accurately measured. A region of the biosensor 200 where the temperature of the sample separated and collected from a body is accurately measured is the sample inlet 210. The sample inlet 210 is a region where a sample is directly collected because it is highly likely that the temperature of the sample measured at the sample inlet 210 is not different from a temperature of the body.

The sample inlet 210 according to an exemplary embodiment is a part of the reagent pad, and when the sample is put into the sample inlet 210, components of the sample move from the sample inlet 210 to a reacting region (a region of the reagent pad is a region including a control line and a test line) via an immunochromatogrpahy method. Accordingly, the sample inlet 210 and the reacting region may maintain a distance. If the sample inlet 210 and the reacting region are quite close to each other and the sample directly contacts the reacting region, a reagent reaction at the control line and the test line, which are the reacting region, may not be properly obtained.

The sample inlet 210 may receive (collect) the sample via any one of various methods. As shown in FIG. 2, a sample may be put into the sample inlet 210 of the biosensor 200 by dropping the sample by using a spuit or by directly dipping the biosensor 200 in a liquid sample.

Figure 3:
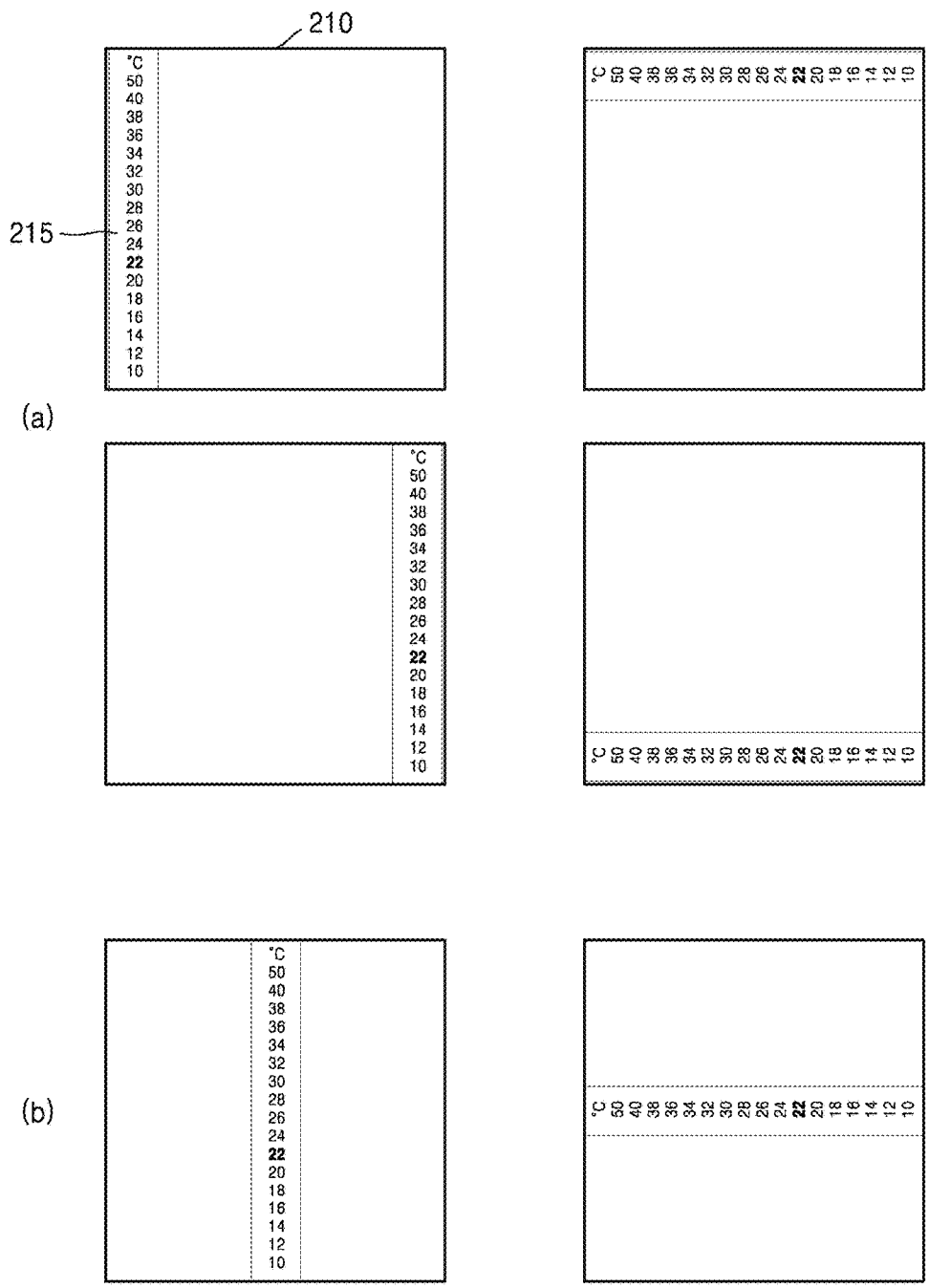
FIG. 3 is a diagram illustrating various locations of a temperature measurer, according to exemplary embodiments.

FIG. 3 is a diagram illustrating various locations of the temperature measurer 215, according to exemplary embodiments.

As shown in FIG. 3, the temperature measurer 215 may be attached to the sample inlet 210 in various manners. In FIG. 3, the temperature measurer 215 is attached to the sample inlet 210 in a form of a temperature tape, but the temperature measurer 215 is not limited thereto, and may be in any one of various forms.

As shown in portion (a) of FIG. 3, the temperature measurer 215 is attached to an edge of the sample inlet 210. The temperature measurer 215 may measure a temperature in a range and display the measured temperature using gradations or calibrations. The temperature measurer 215 may be configured to display a color which changes according to temperatures.

To change a color according to temperatures, the temperature measurer 215 may use a thermochromic ink. For example, a thermochromic ink may be applied on a surface of a beer can such that a color of the surface changes into a color, thereby notifying a consumer of an adequate temperature. The thermochromic ink is prepared by mixing thermosensitive discoloration materials that discolor at a temperature. Examples of the thermochromic ink may include a color reversible ink that discolors and then recovers to an original color according to temperature and a nonreversible ink that does not recover to an original color after discoloration. The temperature measurer 215 according to an exemplary embodiment may use a color reversible ink for determining a temperature of a sample. Such a thermochromic ink may be prepared by using a stilbene derivative that is an organic compound as a raw material.

The temperature measurer 215 according to an exemplary embodiment may be printed in a form of a linear tape using thermochromic inks corresponding to gradations of measurable temperature ranges, and when a sample is put into the sample inlet 210, the temperature measurer 215 may discolor at a temperature such that a user is able to determine a temperature of the sample with naked eyes.

As shown in portion (b) of FIG. 3, a temperature measurer is designed to be located at a center of a sample inlet. When a temperature measurer is located at a center of a sample inlet, the temperature measurer may contact a sample in a large area, and a user may easily check a temperature of the sample with naked eyes compared to when a temperature measurer is located at an edge of a sample inlet. However, when a temperature measurer is located at a center of a sample inlet, a movement of a sample when an immunochromatogrpahy method is used may be hindered, and thus the temperature measurer may be located while considering an effect of the location thereof on the movement of the sample.

Figure 4:
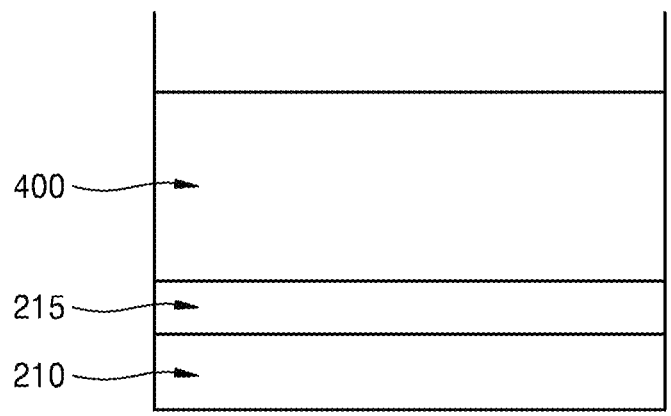
FIG. 4 is a cross-sectional view of a sample inlet of a reagent pad, according to an exemplary embodiment.

FIG. 4 is a cross-sectional view of the sample inlet 210 of a reagent pad, according to an exemplary embodiment.

Referring to FIG. 4, in the reagent pad, the sample inlet 210 and a reacting region are connected to each other, and thus a reagent reaction may be detected via an immunochromatogrpahy method. The temperature measurer 215 for measuring a temperature of a sample 400 is attached to a top of the sample inlet 210 of the reagent pad, such as to directly measure the temperature of the sample 400. In FIG. 4, the sample 400 contacts the temperature measurer 215 and does not contact the sample inlet 210 that is a part of the reagent pad, but it would be obvious to one of ordinary skill in the art that the sample 400 directly contacts the reagent pad for a reagent reaction. Accordingly, the sample 400 may directly contact the sample inlet 210 of the reagent pad, and the temperature measurer 215 may be attached to a top of a partial region of the reagent pad. Details of a method of the temperature measurer 215 have been described above with regard to FIG. 3 regarding the method of using a thermochromic ink.

Figure 5:
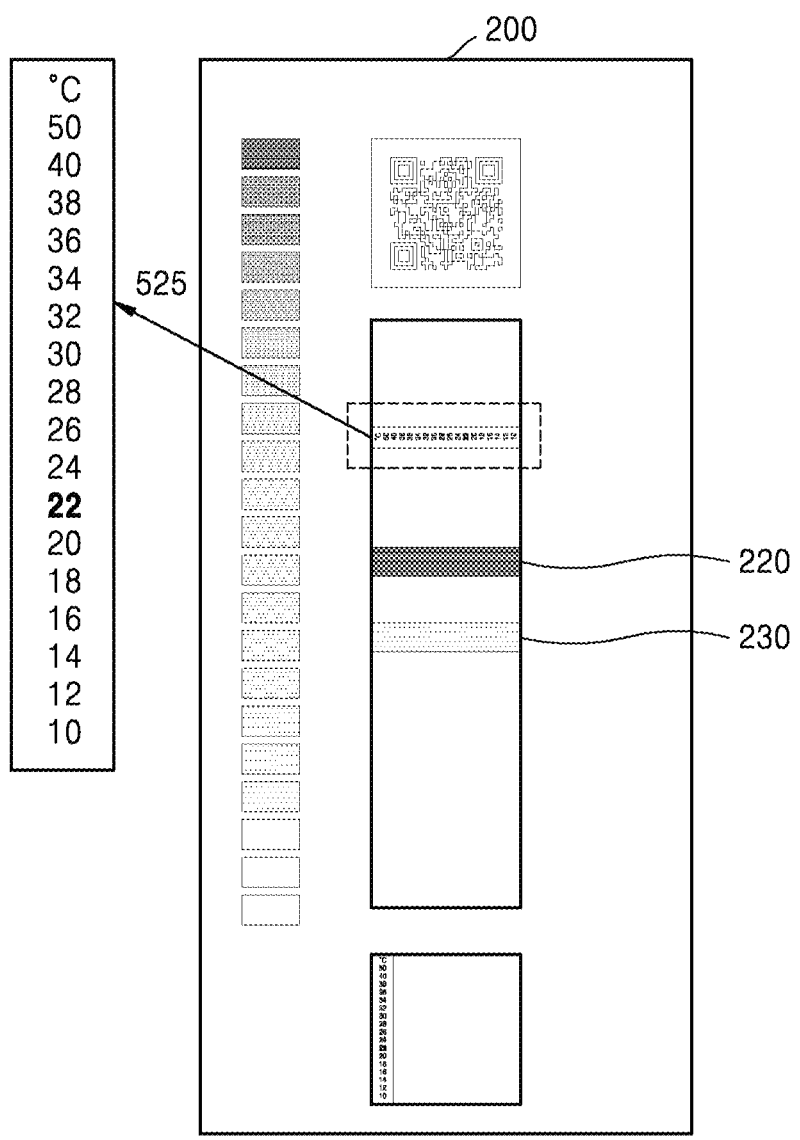
FIG. 5 is a view of a temperature measurer attached to a reacting region of a reagent pad, according to an exemplary embodiment.

FIG. 5 is a view of a temperature measurer 525 attached to a reacting region of a reagent pad, according to an exemplary embodiment.

As shown in FIG. 5, the temperature measurer 525 is designed to be located near a reacting region (e.g., the control line 220 and the test line 230) of the reagent pad. Accordingly, a temperature of a reaction in the test line 230 of the reacting region is measured, and by obtaining the temperature of the reaction, accuracy of deriving a quantitative value of a sample may be increased.

A temperature of a sample in the reacting region where a reaction occurs is a variable in calibrating a quantitative value. Because the temperature in the control line 220 and the test line 230 is a temperature at which a reagent and the sample react with each other to change a color of the test line 230, a theory of a reagent reaction may be applied to measurement when the temperature in the control line 220 and the test line 230 is similar to a temperature of a reagent reaction (a temperature in a quantitative reaction) theoretically obtained in a terminal. The terminal may compare a measured temperature with a temperature in a quantitative reaction and may perform paired-comparison with a quantitative value in the quantitative reaction, thereby reducing an error generated by measurement environmental conditions.

The temperature measurer 525, which are located at the control and test lines 220 and 230 of the reagent pad, may be designed to be located farther than the control line 220 based on a sample inlet. The reacting region may be a whole neighboring area of the control line 220 and the test line 230, and the temperature measurer 525 may be designed to be located farther than the control line 220 such that the temperature measurer 525 does not affect a reagent reaction in an immunochromatogrpahy method. However, a location of the temperature measurer 525 is not limited thereto, and the temperature measurer 525 may be attached near the control line 220 and the test line 230 as long as the temperature measurer 525 does not hinder a reagent reaction between the sample and the test line 230 and the control line 220.

Figure 6:
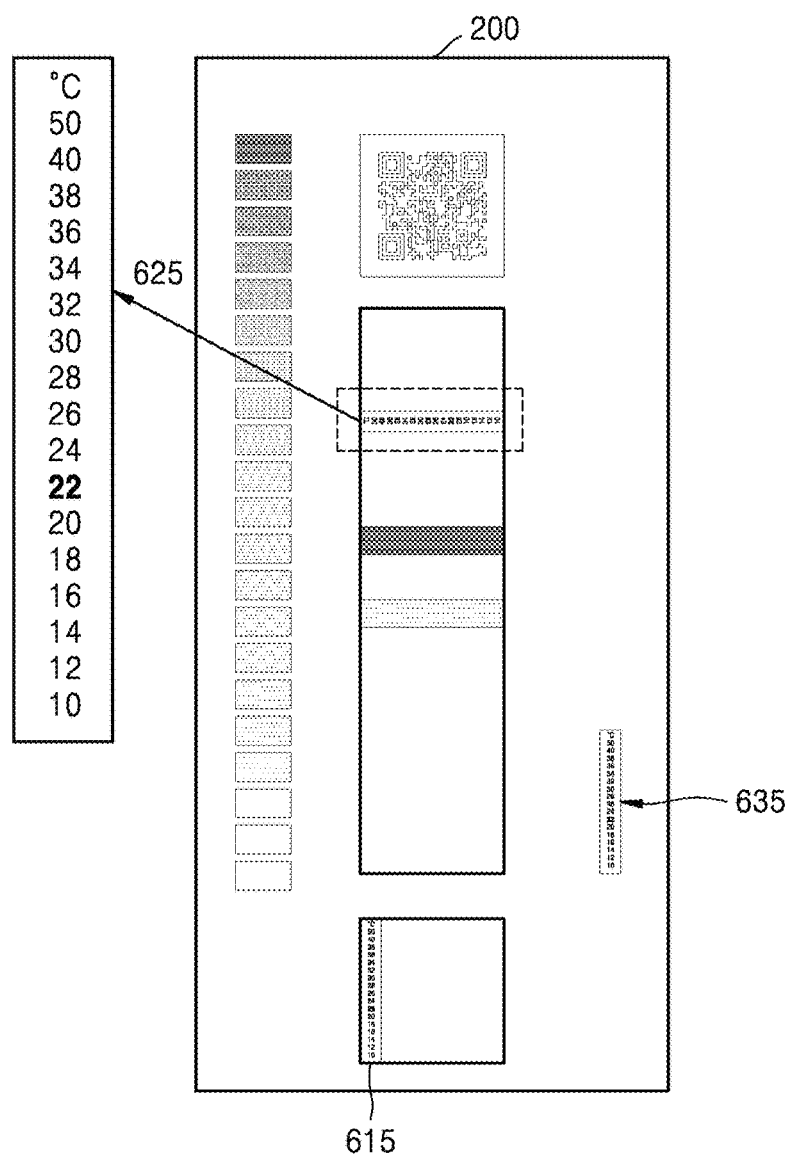
FIG. 6 is a view of a biosensor to which temperature measurers measuring a room temperature are attached, according to exemplary embodiments.

FIG. 6 is a view of the biosensor 200 to which temperature measurers 615, 625, and 635 measuring a room temperature are attached, according to exemplary embodiments.

As shown in FIG. 6, the temperature measurers 615 through 635 may be located at various locations of the biosensor 200. The temperature measurer 615 may be located at a sample inlet to measure a temperature of a sample as described above with reference to FIGS. 2 through 4, or the temperature measurer 625 may be located near a reacting region of a reagent pad to measure a temperature of a reagent reaction as described above with reference to FIG. 5.

In the biosensor 200 according to an exemplary embodiment, the temperature measurer 635 may be attached on the biosensor 200 separately from the reagent pad to measure a room temperature. The temperature measurer 635 attached on the biosensor 200 is not used to measure a temperature of a sample, but may be used to measure a temperature of a place where the reagent reaction is performed, i.e., a room temperature. Accordingly, if a room temperature is measured via another method (for example, if a room temperature is measured by a terminal including a temperature sensor), the temperature measurer 635 attached on the biosensor 200 may not exist.

According to circumstances, the temperature measurer 635 attached on the biosensor 200 may be used to measure a temperature of the reacting region. If the temperature measurer 625 is unable to be attached on the reacting region of the reagent pad, the temperature measurer 635 may be located on the biosensor 200 near the reacting region to measure a temperature of a reagent reaction of a sample.

Figure 7:
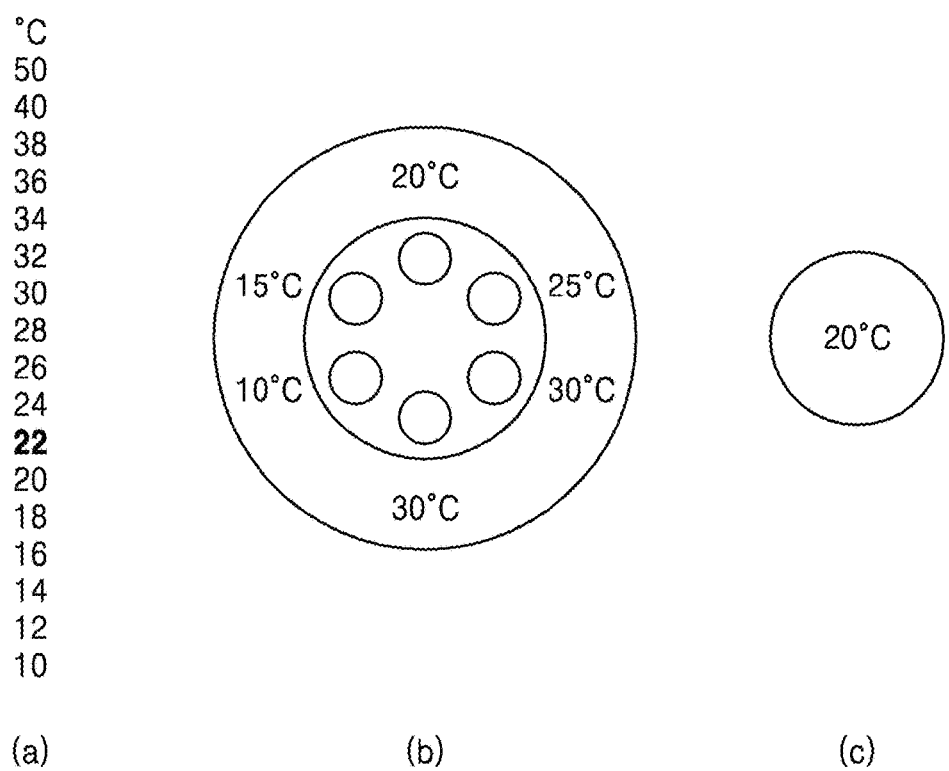
FIG. 7 is a diagram illustrating various types of a temperature measurer, according to exemplary embodiments.

FIG. 7 is a diagram illustrating various types of a temperature measurer, according to exemplary embodiments.

A temperature measurer according to an exemplary embodiment may be attached to a biosensor in any one of various forms. A temperature measurer may be attached on a biosensor in a form of a tape, such as a temperature tape, or may be printed on a biosensor during biosensor manufacturing processes. A temperature tape may be prepared by using a thermochromic ink described above, and a temperature measurer having a color reversible characteristic may be used to measure a temperature of a sample, wherein a color is changed at a temperature equal to or higher than a temperature and an original color is recovered at a temperature lower than the temperature.

As shown in portion (a) of FIG. 7, a linear temperature measurer may be attached on a biosensor. The linear temperature measurer has a form similar to that of a mercury thermometer that is commonly used, and may provide an environment for intuitively measuring a temperature to a user of the biosensor. The linear temperature measurer may display gradations within a measurable temperature range, and a region of the linear temperature measurer corresponding to a measured temperature may discolor to show a value of the measured temperature in a number of a color. As shown in portion (a), when the gradations are displayed at intervals of 2° C. and the measured temperature is 22° C., temperatures of 20° C. and 24° C. near 22° C. that is the measured temperature may be set to be distinguished from 22° C. Also, when three gradations from 20° C. to 24° C. are discolored, the measured temperature may be determined to be an average value of a maximum temperature and a minimum temperature, which are at discolored gradations. A user may variously set discoloration of the linear temperature measurer to determine the measured temperature.

As shown in portion (b) of FIG. 7, a circular temperature measurer may be attached on a biosensor. The circular temperature measurer is obtained by changing a shape the linear temperature measurer of portion (a) to a circle, and because principles thereof are similar to the linear temperature measurer, details thereof are not provided again.

As shown in portion (c) of FIG. 7, a temperature measurer that discolors only at a temperature may be attached on a biosensor. Such a temperature measurer may be used in a limited condition in which a reagent and a sample react with each other at a temperature.

Figure 8:
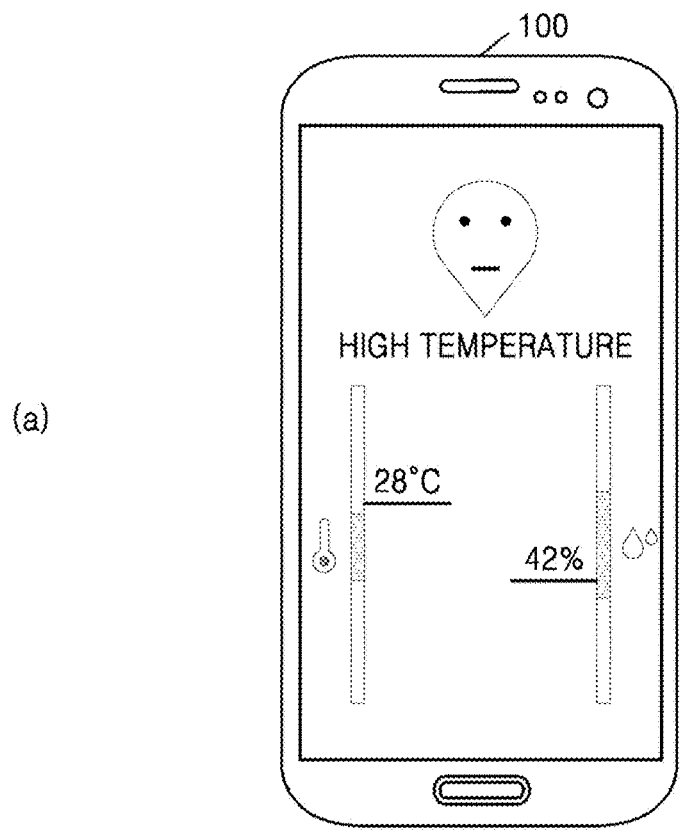
FIG. 8 is a diagram illustrating a temperature measurer of a terminal, according to an exemplary embodiment.
Figure 8:
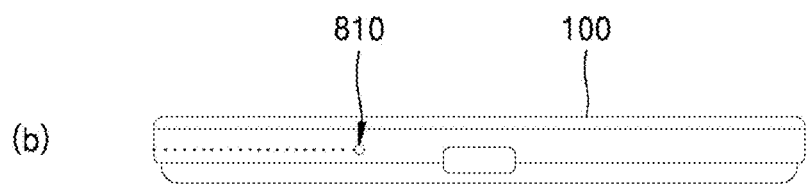

FIG. 8 is a diagram illustrating a temperature measurer of the terminal 100, according to an exemplary embodiment.

Referring to portions (a) and (b) of FIG. 8, the terminal 100 measures a room temperature of an environment in which measurement is performed by using a temperature sensor 810 included in the terminal 100. The terminal 100, such as a smart phone or a tablet PC, usually includes a temperature sensor and a humidity sensor, and a temperature inside or outside the terminal 100 is measured by using the temperature sensor.

As shown in portions (a) and (b) of FIG. 8, the temperature sensor 810 may be located at a location of the terminal 100, and the terminal 100 may determine a room temperature via a measured value input through the temperature sensor 810. Such a temperature sensor 810 may be included in the terminal 100 in any one of various forms, as will now be described in detail with reference to FIG. 9.

Figure 9:
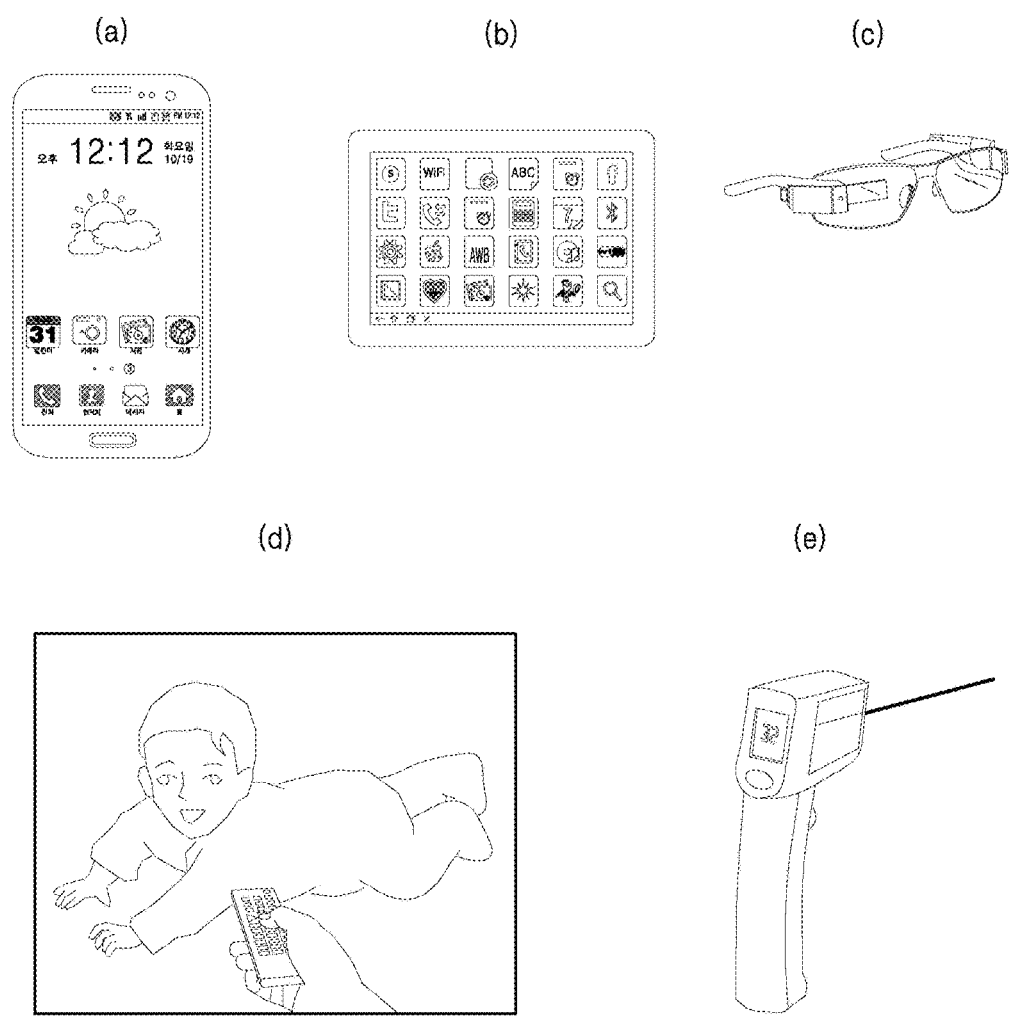
FIG. 9 is a diagram illustrating various devices for measuring a temperature of a sample and a room temperature, according to exemplary embodiments.

FIG. 9 is a diagram illustrating various devices for measuring a temperature of a sample and a room temperature, according to exemplary embodiments.

As shown in portions (a), (b), and (c) of FIG. 9, a temperature measurer may be included in any type of a terminal, such as a smart phone, a tablet PC, or a wearable device, to measure a temperature.

As shown in portion (d) of FIG. 9, a terminal may measure a room temperature by including an infrared ray (IR) thermometer. The IR thermometer measures an IR radiated from an object having heat, and because IR radiation energy radiated from a surface of the object is spread through a space, the IR thermometer may measure a temperature of the object without having to contact the object. Examples of the IR thermometer include a monochromatic type IR thermometer that measures IR radiation energy with respect to a wavelength, and a ratio type IR thermometer that measures a radiation strength ratio of two types of wavelengths. A suitable IR thermometer according to measurement circumstances of a sample may be used. The terminal converts radiation intensity input through an IR detector to heat to increase a temperature of a heat detector, converts a changed temperature of the heat detector to an electronic signal, and amplifies the electronic signal to display the amplified electronic signal as a measured temperature.

As shown in portion (e) of FIG. 9, a terminal may include a laser thermometer to measure a temperature. A laser is a type of light and the laser thermometer may measure a temperature by using a photoconductive or light diode semiconductor. A temperature may be measured based on intensity of light radiated through a change of resistance or a change of current or voltage, which corresponds to a temperature.

In addition, according to an exemplary embodiment, a terminal may include a thermal image camera to measure a temperature via the thermal image camera. Therefore, if a terminal is able to perform a function of measuring a temperature, such a terminal may perform the temperature measurement of the disclosed embodiments.

Figure 10:
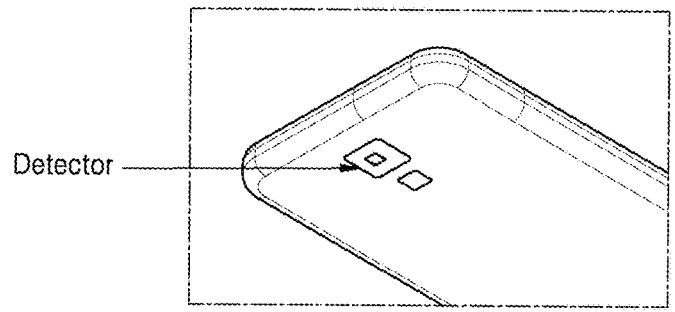
FIG. 10 is a diagram for describing a terminal capturing an image of a biosensor, according to an exemplary embodiment.
Figure 10:
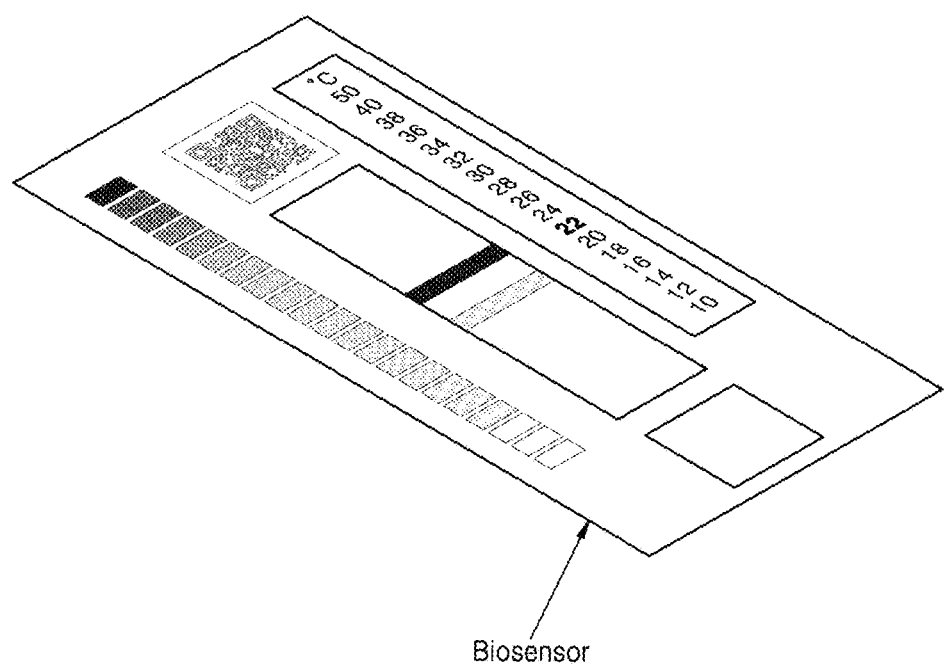

FIG. 10 is a diagram for describing a terminal capturing an image of a biosensor, according to an exemplary embodiment.

After a sample is collected at a sample inlet, the terminal may receive the image of the biosensor by capturing the image of the biosensor. The terminal receives information displayed on the biosensor in a form of an image, and may analyze the received information to determine a reaction result of the sample.

As described above with reference to FIG. 1, the biosensor may display discoloration information in a reacting region of a reagent pad, reference brightness information, and ID information, and the terminal may obtain the information displayed on the biosensor by using a camera sensor or detector. For example, when a temperature measurer for measuring a room temperature is attached on the biosensor and the temperature measurer displays a temperature, the terminal may read the temperature via optical character recognition (OCR).

Upon receiving the image of the biosensor, the terminal may store, together with the image, metadata of the image. When the terminal captures the image of the biosensor by using an optical image sensor (a camera) or detector, the terminal may simultaneously or sequentially measure information about a captured time, a location, a temperature, humidity, atmospheric pressure, and lighting, and store the measured information as metadata of the image. A storage of the terminal may prepare a database (DB) of the metadata according to items, and the items may be used as variables while analyzing the image later.

Also, because the ID information included in the image may include not only ID information of the biosensor itself but also various types of information, the terminal may analyze the ID information to obtain measurement-related information. The ID information will be described in detail later with reference to FIG. 14.

Figure 11:
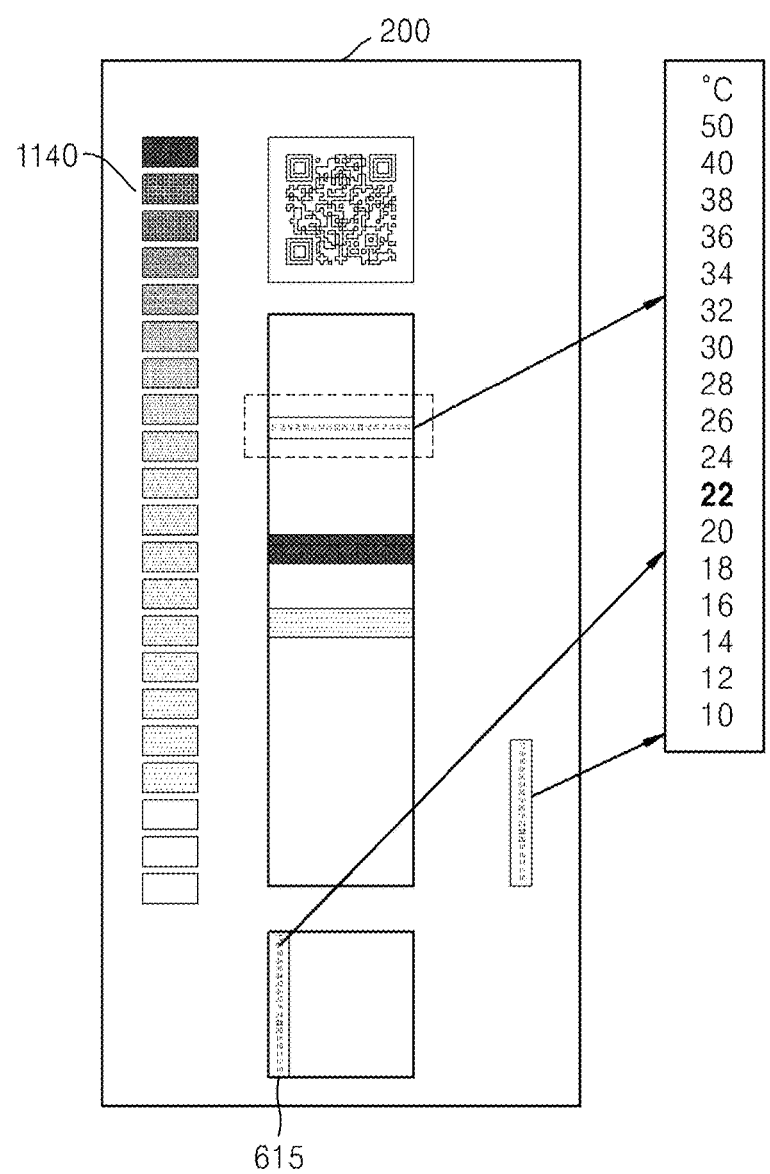
FIG. 11 is a view illustrating a biosensor displaying reference brightness information, according to an exemplary embodiment.

FIG. 11 is a view illustrating the biosensor 200 displaying reference brightness information 1140, according to an exemplary embodiment.

As shown in FIG. 11, the biosensor 200 displays the reference brightness information 1140. The reference brightness information 1140 is information in which a color is arranged according to brightness levels. The color may be the same as or similar to a discolored color of a test line of a reacting region of a reagent pad, which is obtained according to a reaction. Accordingly, when the reaction occurs, brightness information of the discolored color of the test line may be compared with the reference brightness information 1140 to be calibrated.

A terminal may compare the brightness information of the discolored color of the test line with the reference brightness information 1140 displayed on the biosensor 200 and determine a brightness level of the discolored color based on the reference brightness information 1140. A quantitative value of a quantitative reaction may be derived via a level of reference brightness.

The reference brightness information 1140 displayed on the biosensor 200 arranges brightness values of one color according to degrees, and in art fields, brightness is classified in eleven levels, wherein a level of the darkest color is 0 and a level of the brightest color is 10. However, the brightness is not classified into eleven levels only and may be classified into more levels for an accurate comparison.

Also, because brightness is related to reflectivity, actual brightness of a color is a factor, but a lighting environment when measuring brightness of the color is also a factor. Accordingly, brightness of a color in a test line of the biosensor 200 may be compared with the reference brightness information 1140 for calibration.

The reference brightness information 1140 is information displayed on the biosensor 200, and may also change according to lighting. Thus, the terminal may compare brightness of a color in the test line and brightness of the reference brightness information 1140 to calibrate the brightness of the color in the test line such that the lighting does not affect the brightness of the color in the test line.

Figure 12:
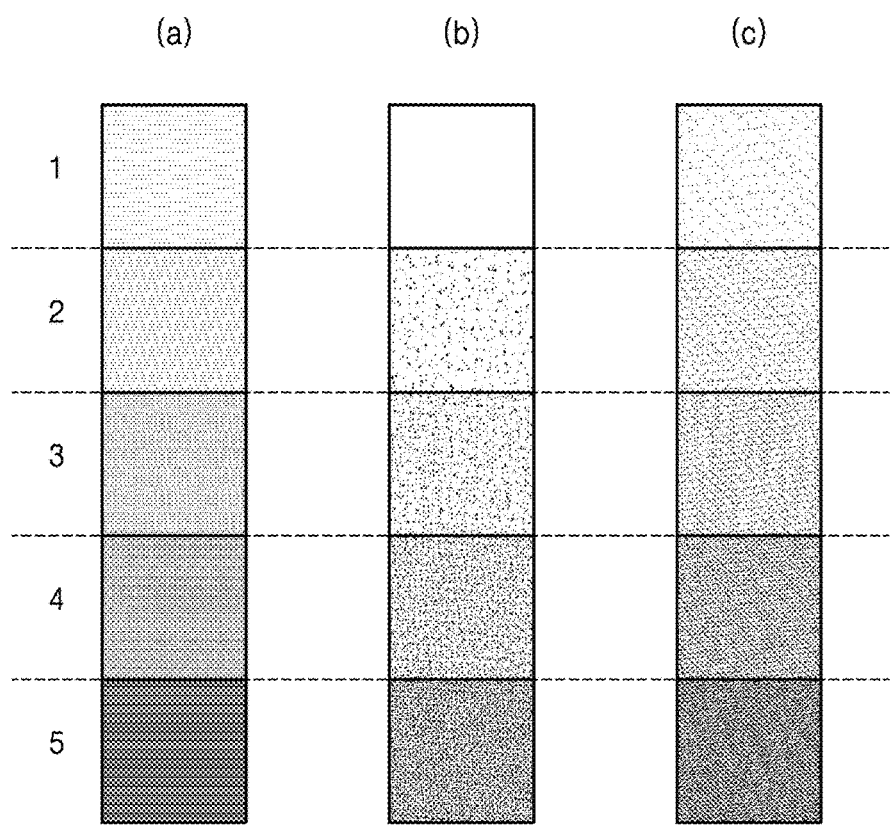
FIG. 12 is a diagram illustrating reference brightness information according to colors, according to exemplary embodiments.

FIG. 12 is a diagram illustrating reference brightness information according to colors, according to exemplary embodiments.

As shown in portions (a), (b), and (c) of FIG. 12, various types of reference brightness information may be displayed on a biosensor. In portions (a), (b), and (c), the reference brightness information is different only in brightness of a color, wherein the color is brighter from 5 to 1.

As shown in portion (a) of FIG. 12, brightness of a first color may be variously classified and displayed. Here, the brightness is classified into five levels, from a first level to a fifth level, wherein the first level is the brightest level. Alternatively, the brightness may be classified into at least two levels and a brightness level that is closest to brightness of a discolored color of a test line may be determined. To determine a closer brightness as possible, brightness levels may be classified as minutely as possible so that a terminal may accurately compare brightness.

A manufacturer of a biosensor may design the biosensor to display reference brightness information of at least two colors. If the number of types of reagent pads used in reaction is at least two, reference brightness information of at least two colors may be displayed, but reference brightness information of at least two colors may also be displayed for one reagent reaction to derive a quantitative value via accurate brightness comparison. For example, when a discolored color after a reaction on a reagent pad is green, reference brightness information of green may be displayed on a biosensor, and at the same time, reference brightness information of yellow or blue, which has high color similarity to green, may be displayed to provide various standards for brightness comparison, thereby increasing accuracy of the brightness comparison.

Figure 13:
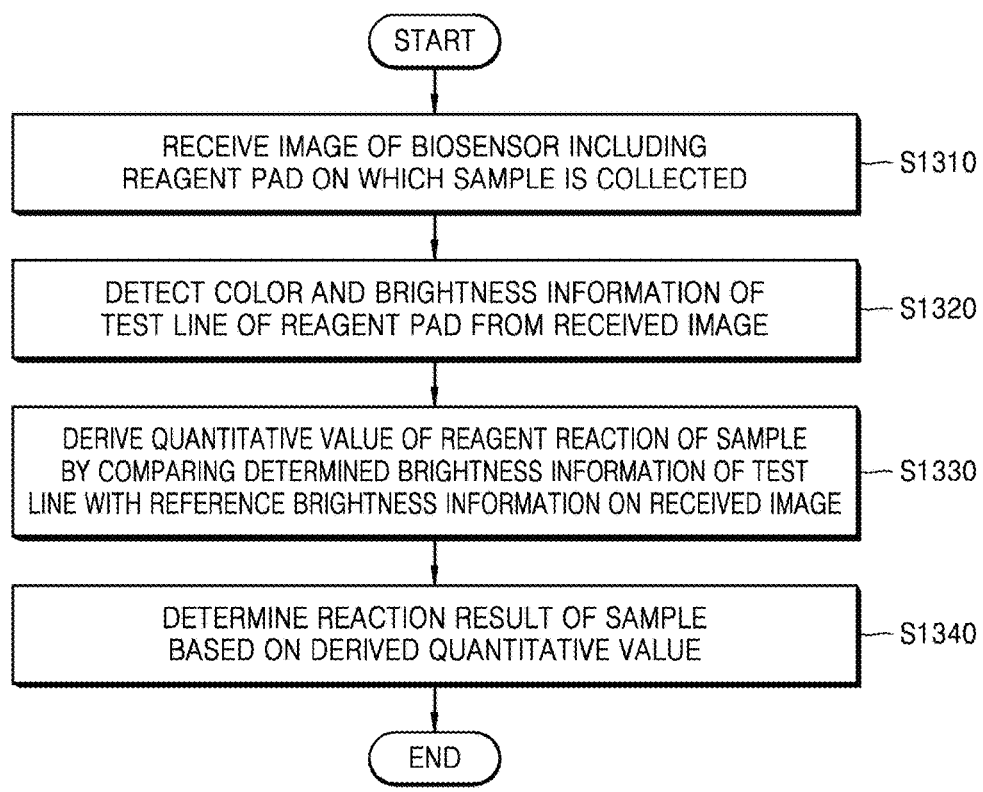
FIG. 13 is a flowchart of a method of measuring, by a terminal, biometric information by using an image of a biosensor, according to an exemplary embodiment.

FIG. 13 is a flowchart of a method of measuring, by a terminal, biometric information by using an image of a biosensor, according to an exemplary embodiment.

In operation S1310, the terminal receives an image of a biosensor (for example, a urine diagnosis strip) including a reagent pad on which a sample is collected. For example, the terminal may obtain the image of the biosensor by using an optical image sensor (a camera). The image may include at least one of discoloration information in a reacting region of the reagent pad, reference brightness information, and ID information. As shown in portions (a), (b), and (c) of FIG. 15, the ID information may be displayed in a QR code, a barcode, or text. Accordingly, the terminal may obtain various types of information regarding a reagent reaction by analyzing the received image.

In operation S1320, the terminal detects color and brightness information of a test line of the reagent pad from the received image.

The terminal may determine discoloration of the test line of the reacting region on the received image. For example, the test line may be discolored from white to red after the reagent reaction, and the terminal may determine the discoloration by using an RGB value or a CMYK value corresponding to a color of the test line.

Also, the terminal may detect the brightness of the color. The detected brightness may be determined in a range from the darkest level (black) to the brightest level (white), and the storage of the terminal may pre-store information corresponding to brightness levels of each color. Alternatively, the storage of the terminal may pre-receive, from a server, and store information corresponding to brightness levels of each color.

In operation S1330, the terminal compares the detected or determined brightness information of the test line with the reference brightness information in the received image to derive a quantitative value of the reagent reaction of the sample.

The terminal may detect the color and the brightness in operation S1320. The terminal may pre-store brightness of the test line in a fixed quantity reaction. The terminal may derive the quantitative value corresponding to the reagent reaction by comparing the brightness in the fixed quantity reaction and the detected brightness of the test line. The storage of the terminal may pre-store information about brightness in the fixed quantity reaction. Alternatively, the terminal may request an external device for such information and then receive the information from the external device.

Whether the quantitative value increases or decreases according to the brightness of the test line may be determined according to a type of the sample. The terminal may detect brightness that is the same as or most similar to the detected brightness of the test line from reference brightness information of a color that is the same as the detected color of the test line.

A detection error generated by lighting may be reduced by using the reference brightness information displayed around the reacting region of the biosensor. Thus, when the lighting changes, the reference brightness information and the detected brightness of the test line are both changed at the same time, and thus the detection error generated by an external environment may be reduced. According to a color correcting method, a factor, such as external lighting, is not considered when comparing a reference color and a color of a test line, and thus, a terminal may wrongly determine a color that is discolored according to an actual reagent reaction. However, according to an exemplary embodiment, because the brightness of the test line and the reference brightness information are compared under the same condition, the detection error generated by external lighting may be decreased.

The terminal may compare the detected brightness and the reference brightness information to derive a relative difference of the detected brightness based on the brightness in the fixed quantity reaction as a quantitative value. For example, the terminal may detect the color of the test line to be red. Also, the terminal may detect that the brightness of the color of the test line, i.e., red, is a second level (i.e., second brightest) from five levels of brightness of the reference brightness information. Meanwhile, in a DB stored in the terminal, the brightness in the fixed quantity reaction may be a third level (i.e., third brightest) among the five levels of brightness of the reference brightness information. Because a difference between the brightness (the second level) of the color of the test line and the brightness (the third level) in the fixed quantity reaction is one level, the terminal may derive the relative difference of the detected brightness (the second level) based on the brightness (the third level) in the fixed quantity reaction as the quantitative value of "one level".

In operation S1340, the terminal determines a reaction result of the sample based on the derived quantitative value. For example, a numerical value corresponding to a sample A may be lower when detected brightness of a test line is brighter. When the detected brightness of the test line is brighter than brightness in a fixed quantity reaction, it may be determined that the numerical value corresponding to the sample A is lower than a reference numerical value. Also, the terminal may derive the numerical value corresponding to the sample A as a reaction result of the sample A. A difference between the derived numerical value and the reference numerical value may correspond to a difference between the detected brightness of the test line and the brightness in the fixed quantity reaction.

Information about brightness in a fixed quantity reaction and reference numerical value of each sample may be pre-stored in the terminal. Alternatively, the terminal may request an external device for such information and receive the information from the external device.

The terminal may detect the color that is changed due to a reaction between the reagent pad and the sample from the received image. The detected color may be stored in an RGB format of value or a CMYK format. Also, the brightness of the detected color may also be detected and stored.

The color and the brightness detected from the received image may be different from actual color and actual brightness of the reagent pad. Thus, to accurately detect the brightness of the test line, the terminal may compare the brightness of the test line of the received image with the reference brightness information of the received image. Also, the relative difference of the brightness of the test line based on the brightness in the fixed quantity reaction may be derived as the quantitative value based on the information about the brightness in the fixed quantity reaction.

The terminal may analyze the reaction result of the collected sample based on the color of the reacting region of the reagent pad and a derived temperature. Because the reacting region includes a control line and the test line, it is determined whether the biosensor is in a normal state based on whether the control line is discolored according to the reagent reaction. Because the control line is subject to discoloration when the sample is input to the control line, if the control line is not discolored even when the sample is input, the biosensor may be determined to operate improperly and incapable of determining a normal reaction. In this case, the terminal may receive the image of the biosensor, in which the control line is not discolored, and notify a user that the biosensor is invalid.

When the test line is discolored according to the reagent reaction, i.e., when a positive reaction is generated in the test line, the terminal may receive the image of the biosensor, in which the test line is discolored. Accordingly, the terminal may perform qualitative detection based on discoloration and perform quantitative detection based on a discoloration level.

The terminal may perform a quantitative analysis according to a discoloration level of the reagent pad of the received image. The quantitative analysis may be performed by comparing the color and the brightness of the test line of the received image with the reference brightness information. The storage of the terminal may store a DB regarding a temperature, a color, and brightness in a fixed quantity reaction, and the terminal may compare the temperature, the color, and the brightness of the test line with the temperature, the color, and the brightness in the DB to detect numerical values of a temperature, a color, and brightness in the reagent reaction. The storage of the terminal, cloud, or a server may store a calibration curve or line value according to each temperature, and thus the numerical values may be calibrated based on a detected temperature.

To further accurately derive the quantitative value and determine the reaction result in operations S1330 and S1340, a temperature measured by a temperature measurer of the biosensor or the terminal may be referred to. Reference temperature information indicating a room temperature may be obtained by using the temperature measurer 635 as described above with reference to FIGS. 6, 8, and 9, or may be obtained by using a temperature sensor of the terminal.

Alternatively, the terminal may obtain the reference temperature information by accessing a network. The terminal may be connected to a network device, such as another terminal or a server, through a communication interface. The terminal may obtain temperature information measured by another terminal that is located in the same room and connected via a network. The terminal may determine a location of the terminal by using a location sensor, such as a global positioning system (GPS), included in the terminal, or by using a Wi-Fi access point (AP) located in the room. Then, the terminal may receive room temperature information according to the location of the terminal from a server of a weather center, and apply the room temperature information as the reference temperature information.

The terminal may not only store discoloration information in a fixed quantity reaction in the storage, but also store adequate temperature information in the fixed quantity reaction in the storage. Because discoloration may vary with temperature according to reagent reaction, a room temperature of a space where a reagent reaction is generated and a temperature of a sample in a reacting region may be variables. For example, when a test line displayed in white before a reagent reaction reacts with a sample, the test line may be discolored to red at a room temperature of 25° C., i.e., an adequate temperature of a fixed quantity reaction, to light red at a temperature of 15° C. that is lower than the room temperature, and to dark red at a temperature of 35° C. that is higher than the room temperature. As another example, the test line may be discolored to blue in the reagent reaction when a temperature of the sample is 25° C., but may be discolored to a different color in a reaction different from a fixed quantity reaction as the sample itself reacts chemically at a higher temperature, for example, 35° C.

Accordingly, the terminal may detect the quantitative value by comparing the discoloration information, the brightness, and the temperature of the reagent reaction on the received image with the discoloration, the brightness, and the temperature in the fixed quantity reaction. The terminal may detect the quantitative value by matching a result of the reagent reaction with data in a DB in which the data are classified according to reference brightness information and temperature information of discoloration.

Figure 14:
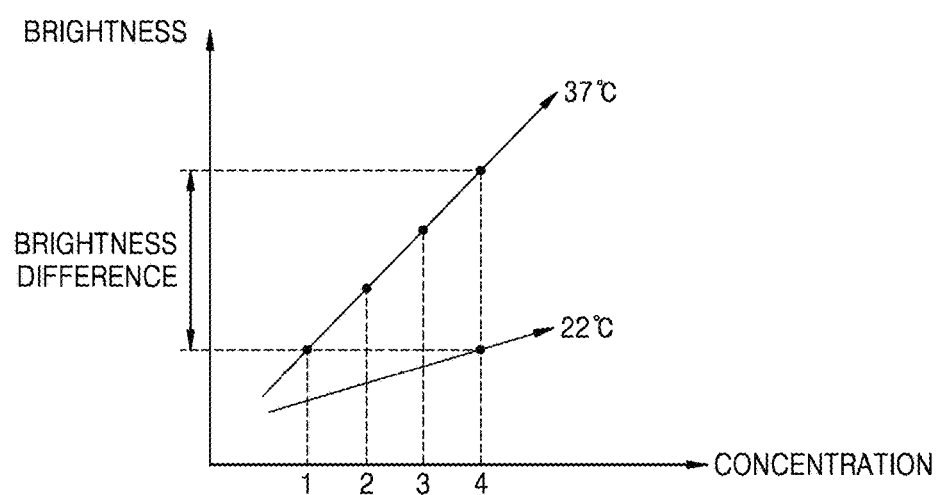
FIG. 14 is a graph showing a brightness value according to a temperature of a sample, according to an exemplary embodiment.

FIG. 14 is a graph showing a brightness value according to a temperature of a sample, according to an exemplary embodiment.

A discoloration level of each sample may vary according to temperatures. As described above, information about color and brightness according to temperatures may be stored in a terminal or cloud (a server), or received from another terminal. The terminal may compare the color and the brightness according to temperatures with the stored information to derive a quantitative value corresponding to a reagent reaction.

For example, as shown in FIG. 14, brightness according to concentration at a temperature of 22° C. and brightness according to concentration at a temperature of 37° C. vary with different rates. In this case, if only discoloration and brightness in an image of a biosensor are analyzed, brightness when a temperature of a sample is 22° C. and concentration of the sample is 4 and brightness when the temperature of the sample is 37° C. and the concentration of the sample is 1, are the same, and thus a wrong quantitative value may be derived. However, if the terminal stores a DB of brightness values according to concentration at temperatures of 22° C. and 37° C., the terminal may determine a difference between the brightness when the temperature is 22° C. and the concentration is 4 and the brightness when the temperature is 37° C. and the concentration is 4, and thus an accurate quantitative value may be derived.

Figure 15:
FIG. 15 is a diagram illustrating identification (ID) displays indicating ID information of a biosensor, according to exemplary embodiments.
Figure 15:

FIG. 15 is a diagram illustrating ID displays indicating ID information of a biosensor, according to exemplary embodiments.

The ID information may be displayed in a form of a QR code as shown in portion (a) of FIG. 15 or in a form of a barcode as shown in portion (b) of FIG. 15. Alternatively, the ID information may be displayed in a form of text including a number and/or a character as shown in portion (c) of FIG. 15. The ID information may be displayed in a form of an image, such as a symbol. The ID information is not limited as long as it is displayed in a form identifiable by the biosensor.

The ID information of the biosensor may include various types of information. The ID information may not only include ID information about the biosensor itself, but may also include information about qualitative/quantitative reaction in the biosensor. The ID information may include information that a test line is discolored to red as a result of a reagent reaction and that a reagent is used to analyze diabetes or protein.

Accordingly, a terminal may analyze the ID information included in a received image of the biosensor to determine information about a purpose of the biosensor, a manufacturer of the biosensor, a manufactured date of the biosensor, and an expiration date of the biosensor.

Such information may be determined by analyzing the displayed ID information, or by using a DB stored in a storage of the terminal that analyzed the ID information. In other words, the information about the purpose, the manufacturer, and the expiration date may be coded and displayed as the ID information, or the terminal may determine the information about the purpose, the manufacturer, and the expiration date by searching the DB pre-stored in the terminal through the ID information.

In addition, the terminal may transmit information related to the ID information to a server, and obtain the information indicated by the ID information from the server. The terminal may request a server related to the manufacturer for additional information regarding the ID information, and the server related to the manufacturer may provide the additional information to the terminal.

In detail, the ID information of the biosensor may include intrinsic information about a user. The user may be a person who provided a sample, i.e., a target. The ID information may include previous measurement information of the user when the user measures biometric information periodically or measure biometric information to diagnose a disease.

For example, when a user wishes to measure a diabetes level through a sample collected on a biosensor, a terminal may obtain ID information by analyzing a received image of the biosensor and transmit the ID information to a hospital server. Upon receiving the ID information, the hospital server may provide information about a past diabetes level of the user to the terminal. Accordingly, the terminal may determine a change in the diabetes level based on the information received from the hospital server. A method of obtaining various types of information by using a server will be described in detail below.

Figure 16:
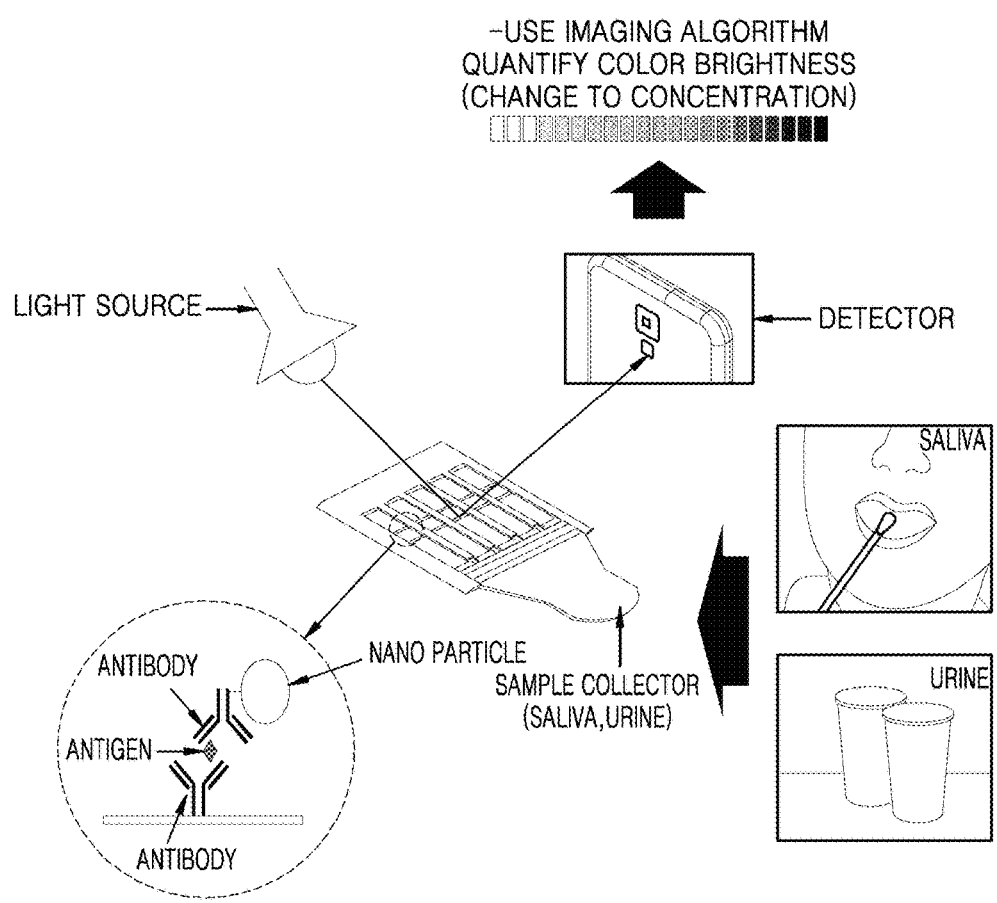
FIG. 16 is a diagram for describing a reagent pad reacting with a sample, according to an exemplary embodiment.

FIG. 16 is a diagram for describing a reagent pad reacting with a sample, according to an exemplary embodiment.

As shown in FIG. 16, an antigen-antibody reaction is generated in a reacting region of the reagent pad. A control line and a test line including an antigen or an antibody may be printed on the reacting region. A reaction with the sample that is input to the reacting region may occur in the control line and the test line. A light source exists in a space where the reaction is generated. For example, when the reaction is generated inside a building, an artificial light, such as a fluorescent lamp, may exist. Because a terminal obtains an image of a biosensor where the reaction is generated, a color or brightness of the image may be different from an actual color or actual brightness based on the light source.

Because the terminal detects biometric information based on discoloration of the control line and the test line of the image of the biosensor, the detected biometric information may vary based on the discoloration and brightness of the control line and the test line. In detail, as shown in FIG. 16, when several reagent reactions are performed by using one sample (e.g., a nano particle of saliva or urine), discoloration and brightness may vary according to the reagent reactions, and thus a detected quantitative value may be calibrated.

A method of calibrating a quantitative value according to a temperature will now be described as one of methods of calibrating a quantitative value.

Figure 17:
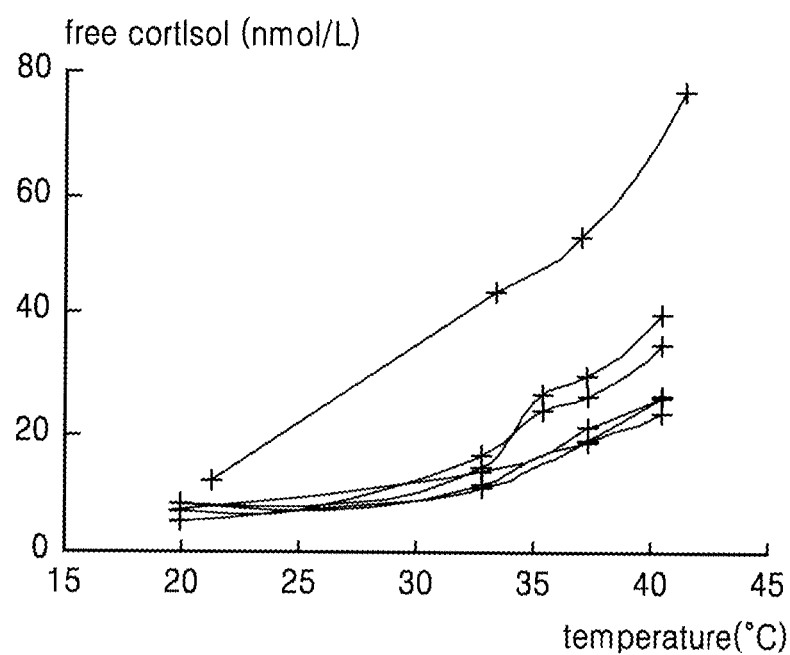
FIG. 17 is a graph showing a result product obtained as a reagent pad reacts with a sample changing according to temperatures, according to an exemplary embodiment.

FIG. 17 is a graph showing a result product obtained as a reagent pad reacts with a sample changing according to temperatures, according to an exemplary embodiment.

A reaction temperature may also be a variable that affects a reaction result in a reagent reaction. FIG. 17 is a graph showing a quantitative value according to reaction temperatures of stress hormone cortisol. In the graph of FIG. 17, quantitative values according to reaction temperatures of stress hormone cortisol are measured for a total of six patients, and as a reaction temperature increases, an amount of stress due to hormone cortisol increases.

According to FIG. 17, a quantitative value changes as a reaction speed of an antigen and an antibody is changed based on a reaction temperature in a fixed quantity reaction, and a quantitative measuring device prevents a quantitative value from varying by uniformly maintaining a temperature. However, a terminal according to an exemplary embodiment is a small terminal that is easily carried, and thus it is difficult to include a device configured to uniformly maintain a temperature. Thus, the terminal may be difficult to prevent a quantitative value from varying according to temperatures.

A method of calibrating a quantitative value will now be described while describing that a temperature of a sample and a temperature in a fixed quantity reaction may be variables in a reagent reaction.

Figure 18:
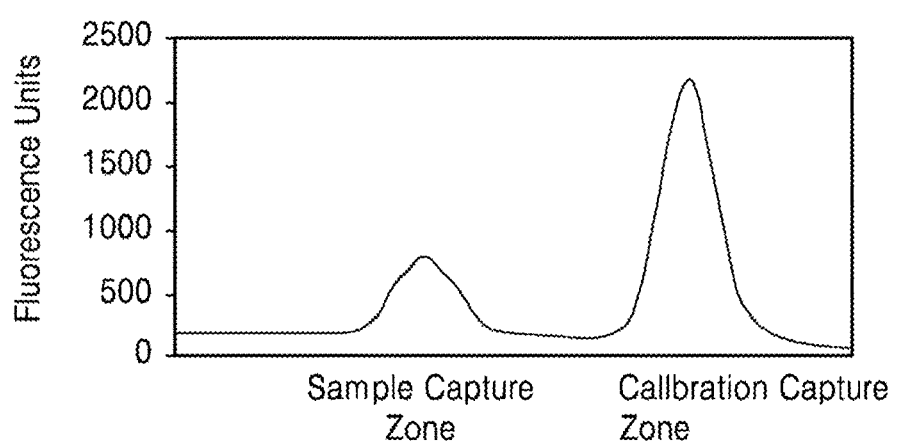
FIG. 18 is a graph showing a temperature of a sample and a calibrated temperature, according to an exemplary embodiment.

FIG. 18 is a graph showing a temperature of a sample and a calibrated temperature, according to an exemplary embodiment. The graph of FIG. 18 shows a result of B-type natriuretic peptide (BNP) assay of a sample, according to an exemplary embodiment. Referring to FIG. 18, fluorescence units corresponding to a sample capture zone and fluorescence units corresponding to a calibration capture zone are different. In other words, a quantitative value corresponding to the sample capture zone that is related to an actual reaction in a test line and a quantitative value corresponding to the calibration capture zone that is related to a fixed quantity reaction, may be different from each other.

Figure 19:
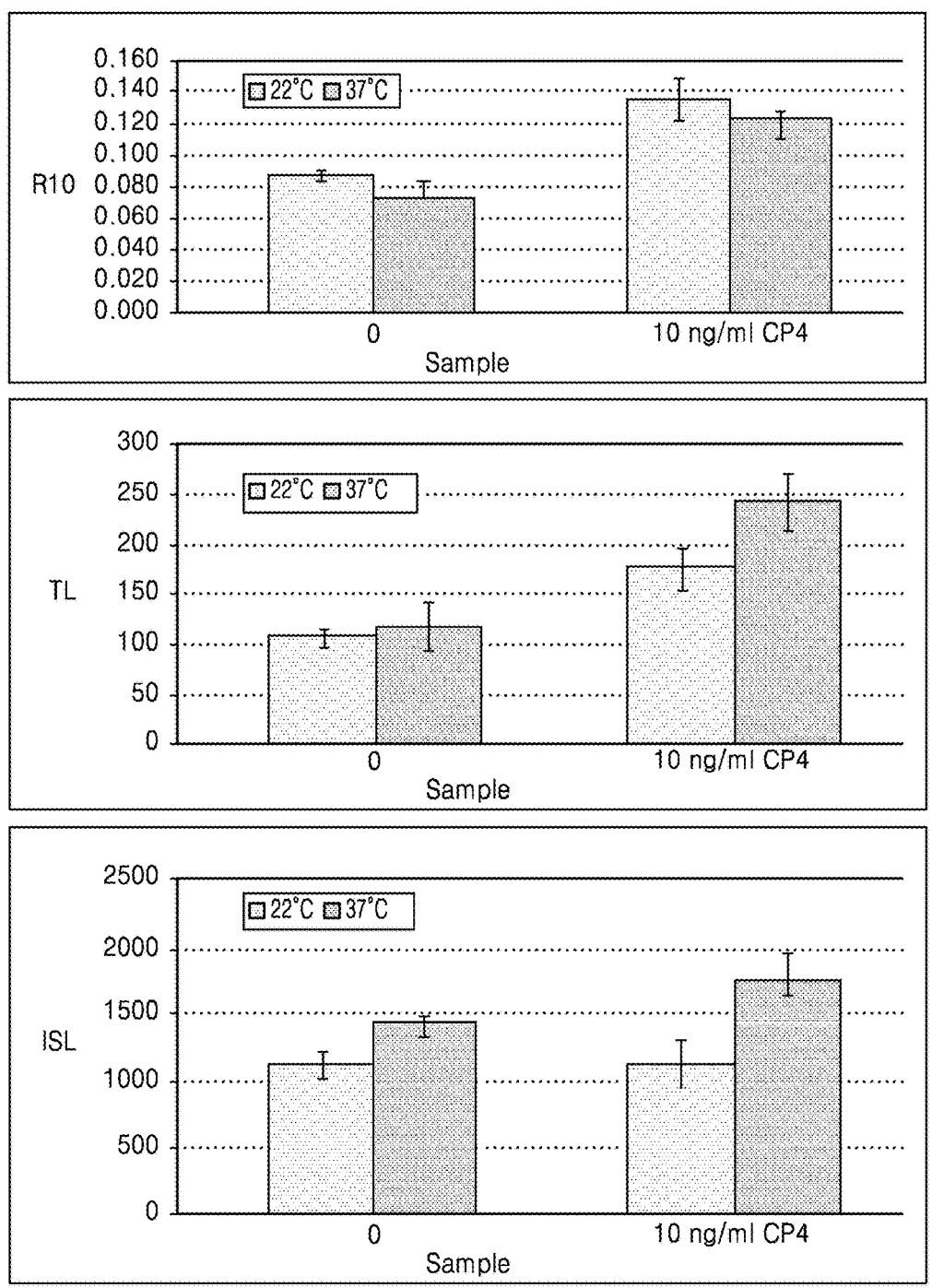
FIGS. 19 and 20 are graphs of a reaction degree varying according to a temperature during a reaction, according to exemplary embodiments.
Figure 20:
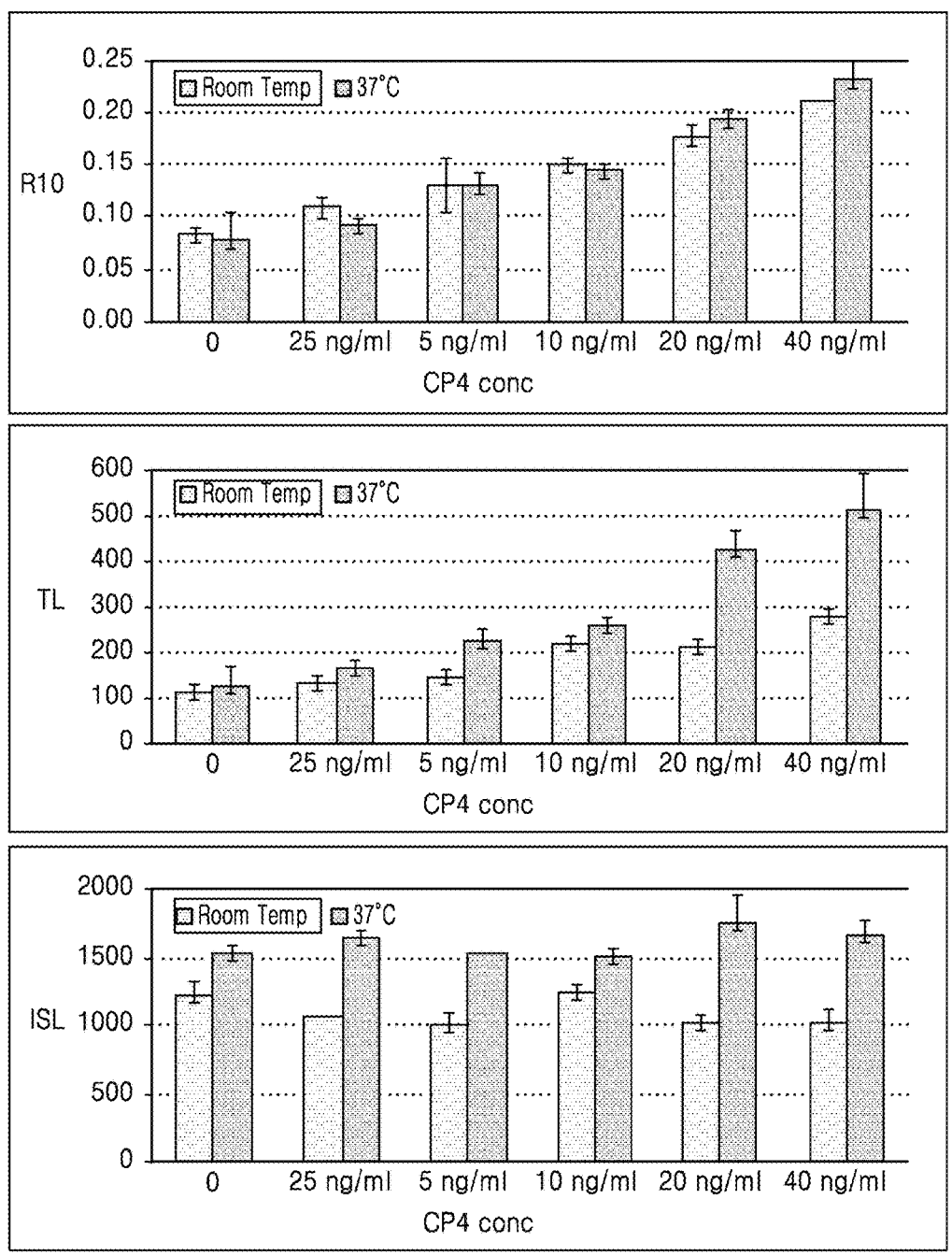

FIGS. 19 and 20 are graphs of values before and after calibrating temperatures of samples, according to exemplary embodiments.

A vertical axis of a top graph of FIG. 19 indicates an R10 value that is a value indicating a ratio of a test line (TL) in a sample capture zone and an internal standard line (ISL) in a calibration capture zone in a fixed quantity reaction, and may be obtained according to Equation 1 below.

$$R10 = \text{Ratio}(TL/TL+ISL) \tag{1}$$

Based on an x-axis of the top graph of FIG. 19, a left vertical bar graph is an R10 value of a reagent when an amount of a sample is 0, and a right vertical bar graph is an R10 value of a reagent when an amount of a sample is 10 ng/ml. Also, a left bar of the vertical bar graph is an R10 value of a reagent when a temperature is 22° C., and a right bar of the vertical bar graph is an R10 value of a reagent when a temperature is 37° C. As shown in the top graph of FIG. 19, an R10 value increases when an amount of a sample increases, and an R10 value decreases when a temperature increases. In other words, a result value of a reagent reaction varies according to temperatures.

A middle graph of FIG. 19 is a graph showing reagent values of a test line (TL), and a bottom graph of FIG. 19 is a graph showing a reagent value of an internal standard line (ISL) in a fixed quantity reaction. In the middle graph of FIG. 19, an amount of a sample increases when a reagent value of the test line increases. Whereas a value of the test line according to temperatures is not significantly different when an amount of sample is 0, a value of the test line according to temperatures largely varies when an amount of sample is 10 ng/ml. Similarly, in the bottom graph of FIG. 19, an ISL value according to temperatures largely varies when an amount of a sample is 10 ng/ml.

A top graph of FIG. 20 shows an R10 value after a temperature is calibrated, with respect to an R10 value of the top graph of FIG. 19. After a temperature is calibrated, an R10 value when a temperature is 22° C. is higher than an R10 value when a temperature is 37° C. when an amount of a sample is 0, the R10 values are similar when the amount of the sample is 5 ng/ml, and the R10 value when the temperature is 37° C. is higher than the R10 value when the temperature is 22° C. when the amount of the sample further increases. As such, the sample is accurately measured by calibrating a quantitative value. A middle graph and a bottom graph of FIG. 20 respectively show a TL value and an ISL value, and also support that the sample is accurately measured via calibration.

Figure 21:
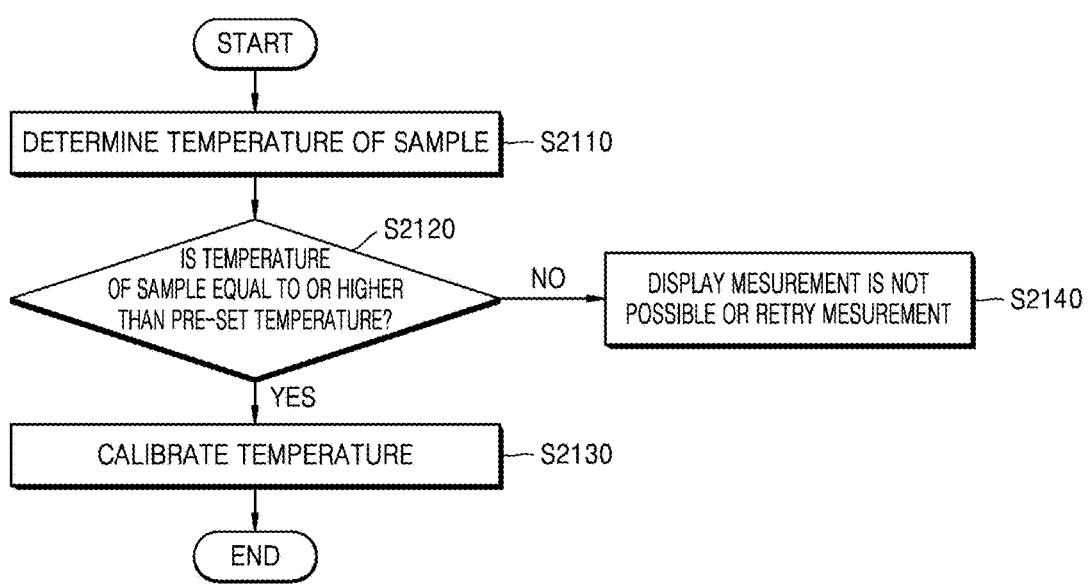
FIGS. 21 and 22 are flowcharts of a method of determining whether a temperature of a sample is within a range of an adequate temperature, according to exemplary embodiments.
Figure 22:
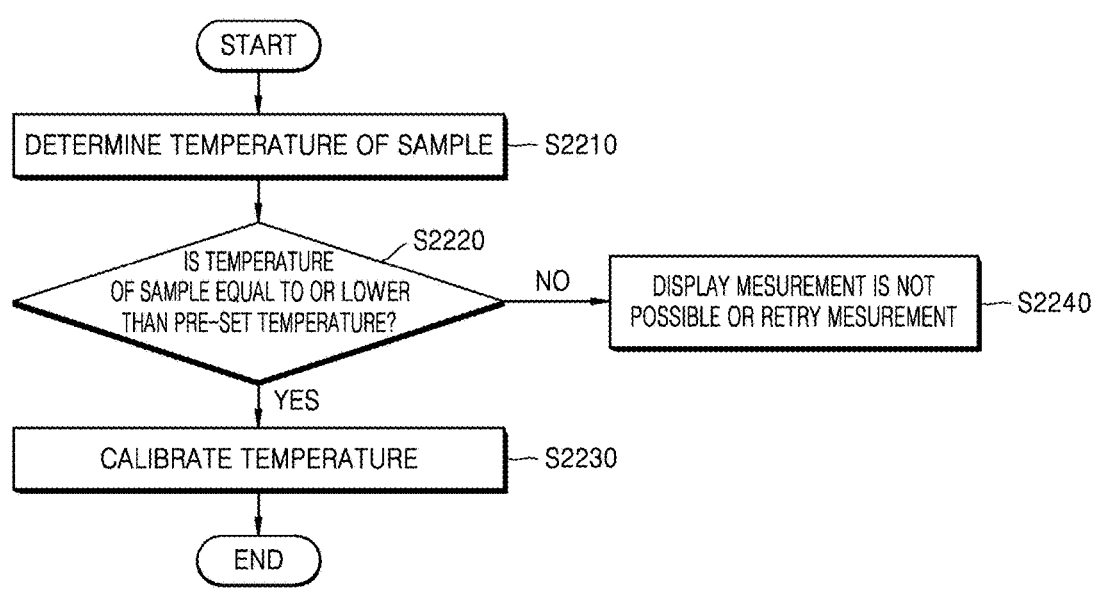

FIGS. 21 and 22 are flowcharts of a method of determining whether a temperature of a sample is within a range of an adequate temperature, according to exemplary embodiments.

As described above, a reagent reaction is an antigen-antibody reaction in which a reaction temperature is a factor. Accordingly, a reaction in a temperature range may enable accurate measurement of a quantitative value, and a normal reaction may not be generated at a temperature outside a range as an antigen or an antibody is changed.

A terminal may determine a temperature of a sample or a reaction temperature by analyzing a received image of a biosensor, and may also obtain a temperature in a fixed quantity reaction via at least one of various routes.

Accordingly, the terminal may determine whether a reagent reaction is valid by comparing a determined temperature of a sample and a pre-set range of an adequate temperature. In operation S2110, the terminal determines the temperature of the sample by analyzing a temperature indicated by a temperature measurer on the received image of the biosensor. For example, when the temperature indicated by the temperature measurer is 22° C., the terminal may determine that the temperature of the sample is 22° C.

In operation S2120, the terminal determines whether the temperature of the sample is equal to or higher than a pre-set temperature. If the sample has a normal reagent reaction at a temperature equal to or higher than 20° C., it is difficult to obtain the normal reagent reaction of the sample when a temperature is 0° C. or 5° C. Thus, the temperature of the sample may be determined to determine whether the normal reagent reaction is obtainable. When the terminal determines that the temperature of the sample is equal to or higher than the pre-set temperature, the terminal proceeds in operation S2130. When the terminal determines that the normal reagent reaction is unable to be obtained, the terminal proceeds in operation S2140.

In operation S2140, the terminal displays, on a display region, a message indicating measurement is not possible or should be retried.

In operation S2130, the terminal obtains a quantitative value by calibrating a temperature, and at this time, accurate measurement may be performed through a color and brightness of a test line.

As in the method of FIG. 21, in the method of FIG. 22, the terminal may be set to calibrate a temperature only when the temperature is lower than or equal to a temperature. Because components of the antigen and the antibody are highly likely to be similar to those of a tissue of a body, when the temperature of the sample exceeds a temperature, the antigen or the antibody may be deformed under a temperature higher than a temperature, and thus the normal reagent reaction may not be obtained. Accordingly, the terminal may be set to perform temperature calibration and measure a fixed quantity reaction when it is determined that the temperature of the sample is lower than or equal to the pre-set temperature.

In operation S2210, the terminal uses the temperature measure on an image of the biosensor to determine the temperature of the sample. Because a method of determining the temperature of the sample has been described above, details thereof are not provided again.

In operation S2220, the terminal determines whether the temperature of the sample is lower than or equal to the pre-set temperature. Because information about the sample may be pre-stored in the storage of the terminal, the range of the adequate temperature of the sample may be determined. The terminal may determine whether the temperature of the sample is higher than an upper limit of the range of the adequate temperature. When the terminal determines that the temperature of the sample is lower than or equal to the pre-set temperature, the terminal proceeds in operation S2230. Otherwise, the terminal proceeds in operation S2240.

In operation S2230, when it is determined that the temperature of the sample is not outside the upper limit of the range of the adequate temperature, i.e., when it is determined that the temperature of the sample is lower than or equal to the upper limit, the terminal calibrates a quantitative value or temperature by comparing the reference brightness information and the brightness of the test line as described above.

In operation S2240, when it is determined that the temperature of the sample is outside the upper limit of the range of the adequate temperature, the terminal displays information that the temperature of the sample is outside the range of the adequate temperature, and a message indicating that measurement is not possible or should be retried.

Figure 23:
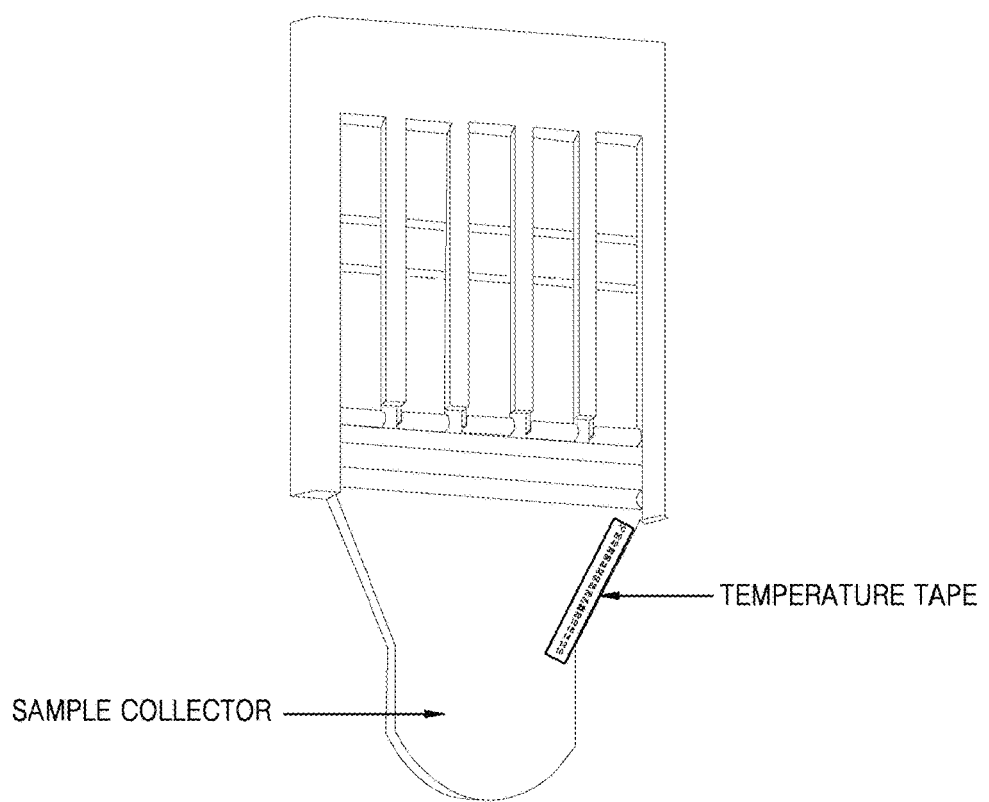
FIG. 23 is a perspective view illustrating a biosensor including a plurality of reagent pads, according to an exemplary embodiment.

FIG. 23 is a perspective view illustrating a biosensor including a plurality of reagent pads, according to an exemplary embodiment.

Hereinabove, a reagent reaction is generated with respect to one sample. However, alternatively, various measurement values may be obtained by simultaneously measuring a plurality of reagent reactions through one sample.

A urine diagnosis strip may be used for measurement for a plurality of reagent reactions, or may be used to briefly measure at least one of various diseases. By attaching the plurality of reagent pads for measuring results of various reagent reactions on the urine diagnosis strip, outbreaks of various diseases may be summarily determined by inputting a urine sample once.

Table 1 below shows an example of a list of diseases that may be determined through a reagent reaction of a sample.

TABLE 1

| | | Item | | | | Positive Finding | |
| --- | --- | --- | --- | --- | --- | --- | --- |
| Tested Target | Screening | Renal disease and uropathy | Urinary tract infection | Hepatabiliary disease | Diabetes | Suspected Disease | Additional Test |
| Occult Blood | ◉ | ◉ | ◉ | ○ | ○ | Renal disease uropathy (excluding nephrotic syndrome), hemoglobinuria, myoglobinuria, menstrual blood contamination | Urinary sediment, specific gravity of urine, BUN, CBC, creatinine, renal function test |

TABLE 1-continued

| Tested Target | Screening | Renal disease and uropathy | Urinary tract infection | Hepatabiliary disease | Diabetes | Suspected Disease | Additional Test |
|---|---|---|---|---|---|---|---|
| Bilirubin | ◎ | | | ◎ | | Hepatocellular dysfunction, biliary obstruction | Liver function test |
| Urobilinogen | ◎ | | | ◎ | | Hepatocellular dysfunction, haemolytic anemia | Liver function test, CBC |
| Ketone Body | ◎ | | | | ◎ | Diabetic ketosis, starvation, vomiting, glycogen storage disease, autointoxication | Blood sugar, urine sugar, blood serum, lipid, blood gas |
| Protein | ◎ | ◎ | ◎ | ○ | ◎ | Renal disease, renal failure, overwork, urinary tract infection, physiological proteinuria | Urinary sediment, specific gravity of urine, BUN, creatine, renal function test |
| Nitrite | ◎ | ○ | ◎ | | ○ | Cystitis, nephropyelitis | Urinary sediment, urinary bacterial test |
| Glucose | ◎ | ◎ | ○ | ○ | ◎ | Diabetes, renal glicosuria, pancreatitis, pregnancy intracerebral hemorrhage, hyperthyroidism | Blood sugar, glucose tolerance test |
| pH | ◎ | ◎ | ◎ | ○ | ○ | Acid: severe diabetes, gout, starvation, nephritis, dehydration, lithiasis Alkaline: urinary tract infection, lithiasis, hyperventilation, vomiting | Urinary sediment, clinical chemical test, blood gas |
| Specific Gravity | ◎ | ◎ | ◎ | ◎ | ◎ | Low specific gravity: overhydration, renal failure, diuresis, diabetes insipidus, nephropyelitis High specific gravity: dipsotherapy, dehydration, diabetes | Urinary sediment, renal function test, urinary bacterial test, hormone measurement Blood sugar, plasma osmotic pressure |
| Leukocyte | ◎ | ○ | ◎ | | ○ | Cystitis, nephropyelitis, aseptic pyuria | Urinary sediment, urinary bacterial test, CBC |

Because different reagents are used for different diseases as shown in Table 1, the reagent pads may be discolored to different colors. Even when the reagent pads are discolored to the same color, brightness of the color may be different. The terminal may have information about discoloration and brightness of colors in advance in the storage, and may analyze a received image of the biosensor by comparing discoloration and brightness of the received image and discoloration and brightness in a normal positive reaction to calibrate a result of fixed quantity reaction.

Examples of diagnosing a disease by using information about discoloration of a reagent pad of a urine diagnosis strip and by selectively using information about brightness will now be described.

Regarding an occult blood (hematuresis) reagent reaction, a reagent pad may be discolored to green when a user has hematuresis. Here, a urine sample of the user contains red blood cells, which means that the user may have kidney problem or bleeding occurred in the urinary tract.

Regarding a bilirubin reagent reaction, malfunction in a liver or a kidney, or discharge of bile may be determined. When a reagent pad is discolored to red, a urine sample of a user includes bilirubin, which suggests that liver cells of the user are damaged or the user may have biliary atresia.

Regarding an urobilinogen reagent reaction, when urobilinogen is detected in a urine sample of a user due to malfunction of a liver or a kidney, a reagent pad is discolored to red.

Regarding a ketone body reagent reaction, when a urine sample of a user contains lots of bubbles, the urine sample may include many protein components. If the user is tired or starving, ketonic acid is generated in the user's body, thereby decreasing the pH in urine. Then, an amount of gas dissolved in urine is increased, bubbles are generated, and thus, a reagent pad is discolored into dark purple.

Regarding a protein reaction, when a reagent pad is discolored to dark green, it may be determined that a protein discharge amount is increased due to malfunction of a kidney. Normally, less than 150 mg of protein is discharged through urine per day. When more than 150 mg of protein is discharged through urine per day, a user may be suffer from proteinuria. When the kidneys of the user malfunction, an amount of protein in urine may increase, and when the user has a bad condition of chronic nephrities, nephrotic syndrome, or diabetic acidosis, the amount of protein in urine is further increased, thereby discoloring the reagent pad to dark green.

Regarding a nitrite (urinary tract bacterial infection) reagent reaction, it is determined whether urine contains nitrite, and bacteria in the urine may change a nitrate to a nitrite. When the urine contains a nitrite, a test line of a reagent pad is discolored, which indicates that a urinary tract is infected with bacteria.

Regarding a glucose reagent reaction, a user is highly likely to have diabetes if a reagent pad is discolored to dark brown.

Regarding a pH (hydrogen ion concentration) reagent reaction, pH of urine normally has an acid level from 4.6 to 8, and when the pH increases (when a pH value increases), a reagent pad is discolored to green.

Regarding a specific gravity reagent reaction, a material dissolved in urine is measured, and a normal range of a specific gravity is from 1.016 to 1.022.

Regarding a leukocyte reagent reaction, when a leukocyte numerical value is abnormal, a reagent pad is discolored to purple.

Information about discoloration and brightness may be pre-stored in a terminal or may be included in ID information of a biosensor. When such information is not obtained from the terminal or the biosensor, the information may be obtained from a server.

As such, the terminal may receive an image of the urine diagnosis strip on which various reagent reactions are simultaneously performed on one sample, thereby determining various diseases.

Figure 24:
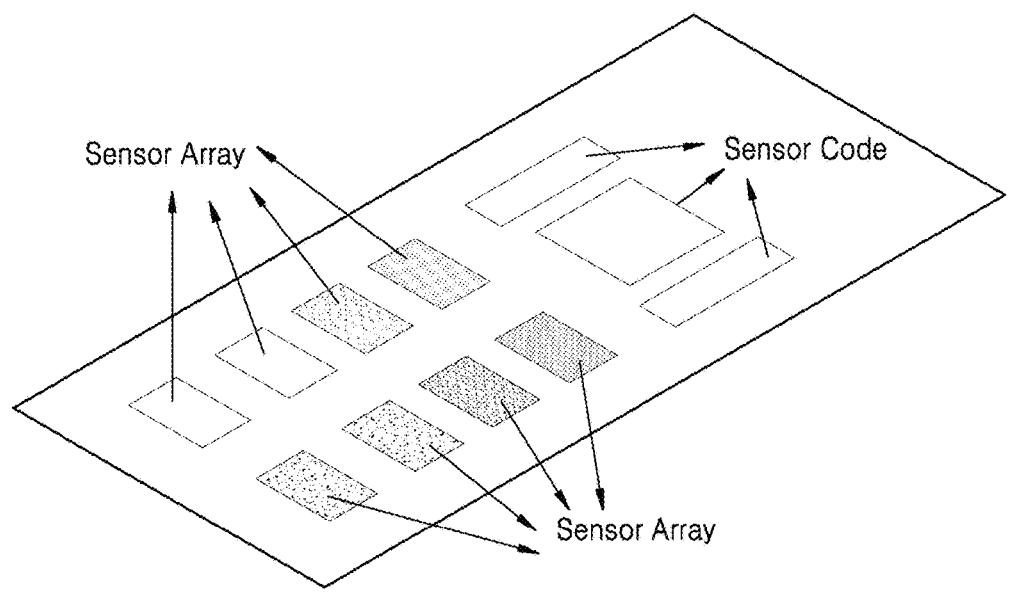
FIG. 24 is a perspective view illustrating a biosensor including a plurality of reagent pads, according to another exemplary embodiment.

FIG. 24 is a perspective view illustrating a biosensor including a plurality of reagent pads, according to another exemplary embodiment.

As described above with reference to FIG. 23, a terminal may measure various types of biometric information by using the biosensor on which various reagent reactions are performed by inputting a sample once. As shown in FIG. 24, the plurality of reagent pads or sensor arrays may be attached to the biosensor. The sample may be input to each of the plurality of reagent pads, or may be input to a common sample inlet of the plurality of reagent pads. As described above, a temperature measurer may be attached to the reagent pad or the biosensor to measure a temperature of the sample and/or a room temperature.

Figure 25:
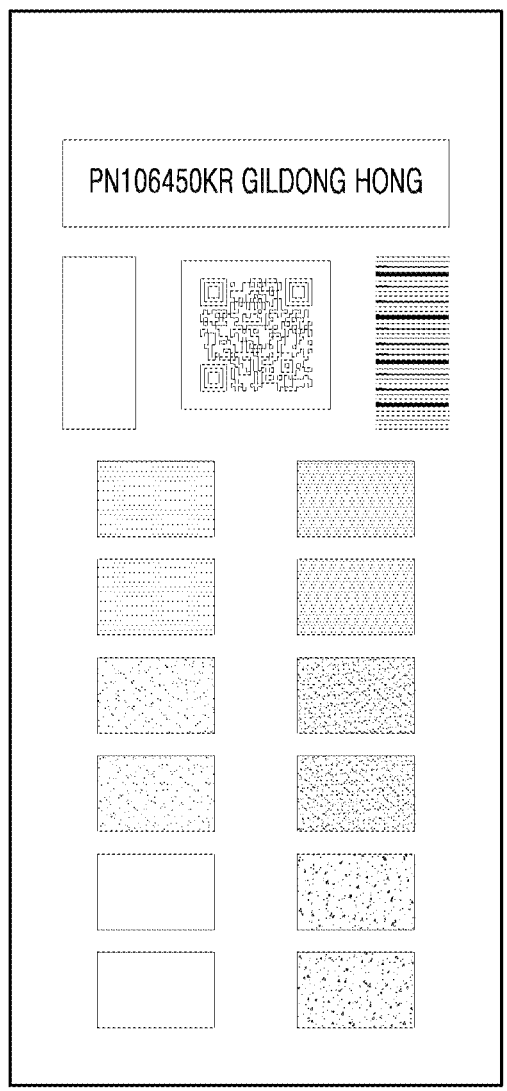
FIG. 25 is a view illustrating a biosensor including a plurality of reagent pads including ID information of the biosensor, according to an exemplary embodiment.

FIG. 25 is a view illustrating a biosensor including a plurality of reagent pads including ID information of the biosensor, according to an exemplary embodiment.

As shown in FIG. 25, the ID information including information about the biosensor is displayed on the biosensor. The biosensor may be identified through the ID information in a form of text, such as "12345-6789 Gildong Hong", or through the ID information in a form of a QR code or a barcode.

In addition, information about an arrangement of the plurality of reagent pads may be used as the ID information. As shown in FIG. 24, eight reagent pads attached on the biosensor may have different colors. The terminal may match locations of the reagent pads having different colors with information about arrangement of a plurality of reagent pads, which is stored in the terminal in advance, to determine the ID information.

A combination of the ID information may vary by changing the locations of the reagent pads attached on the biosensor as well as the colors of the reagent pads, and the terminal may use the locations of the reagent pads as the ID information while receiving and reading an image of the biosensor.

The terminal may use a shape of the biosensor as the ID information of the biosensor. For example, a ratio of a width and a length of the biosensor may be used as the ID information. As another example, a shape of the biosensor, i.e., a rectangular shape or an oval shape of the biosensor may be used as the ID information. As another example, a color of the biosensor may be used as the ID information.

The ID information displayed on the biosensor including the plurality of reagent pads may include information about a reagent reaction of each reagent pad. The ID information may include information about discoloration of a reagent pad as a result of a reagent reaction or information about a reagent reaction, for example, information that the reagent reaction is used to analyze diabetes or protein.

Upon receiving the image of the biosensor including the plurality of reagent pads, the terminal may obtain information about each reagent reaction, and determine a result of the reagent reaction based on a color and brightness of the reagent reaction. When the reagent pad is discolored as a positive reaction, a qualitative determination may be performed based on the discoloration to determine existence of a disease, or a quantitative determination may be performed based on brightness (darkness) of a color of the discoloration.

Figure 26:
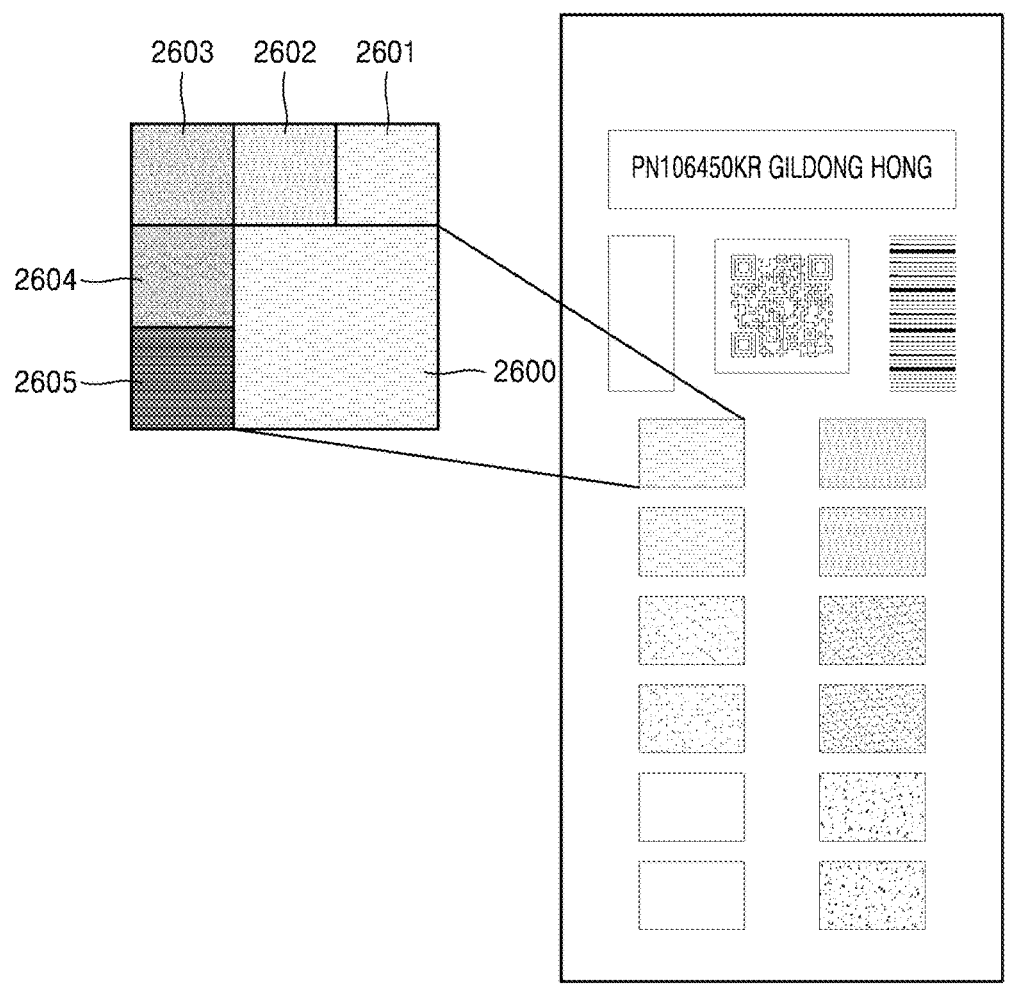
FIG. 26 is a view illustrating a biosensor displaying reference brightness information around a reagent pad, according to an exemplary embodiment.

FIG. 26 is a view illustrating a biosensor displaying reference brightness information around a reagent pad 2600, according to an exemplary embodiment.

The reference brightness information of each of a plurality of reagent pads may be displayed on the biosensor. The reagent pads may be discolored into different colors based on reagent reactions, and a terminal may receive brightness information of the discolored colors as an image and calibrate a quantitative value based on the brightness information to perform an accurate measurement.

As shown in FIG. 26, the reference brightness information including various types of reference brightness information 2601 through 2605 about a discolored color with respect to the reagent pad 2600, may be displayed. For example, when the reagent pad 2600 is discolored to blue as a result of a reagent reaction, wherein a brightness level of the blue is a first level (brightest level) among five levels. The biosensor may display the reference brightness information 2601 through 2605 having the first through fifth levels of the blue around the reagent pad 2600.

The terminal may receive information about a color and brightness of the reagent pad 2600 and the reference brightness information 2601 through 2605. The terminal may obtain, as a quantitative value, a relative difference of brightness of the reagent pad 2600 based on brightness in a fixed quantity reaction. The terminal may calibrate the brightness of the reagent pad 2600 by using the reference brightness information 2601 through 2605. When lighting of a space where measurement is performed is bright, the brightness of the reagent pad 2600 and the reference brightness information 2601 through 2605 are also measured to be bright compared to when the lighting is dark.

Because the terminal pre-stores brightness information of a reagent reaction in a fixed quantity reaction, calibration may be performed by using the brightness information in the fixed quantity reaction. For example, a brightness level of a region of reference brightness information pre-stored in a terminal may be a second level, whereas a brightness level of a region of reference brightness information in an image of a biosensor obtained by the terminal is a first level, wherein the region corresponds to a fixed quantity reaction. Also, the first level may be brighter than the second level. In addition, a brightness level of a reagent pad from the image of the biosensor may be a first level. The terminal may change the brightness level of the region of the reference brightness information in the image of the biosensor from the first level to the second level, and may also change the brightness level of the reagent pad from the first level to the second level. As such, the terminal may calibrate the brightness level of the reagent pad by using the brightness level in the fixed quantity reaction, which is pre-stored.

Because the calibrated brightness level of the reagent pad is the second level (even if the brightness level of the reagent pad in the image is the first level), the terminal may determine that a quantitative value corresponding to the reagent reaction and a quantitative value corresponding to the fixed quantity reaction are the same. Accordingly, the terminal may determine a reaction result to be a positive reaction. Also, the terminal may specify existence of a disease or a related numerical value based on the positive reaction.

As another example, a brightness level in a fixed quantity reaction may be a third level among five levels, and information that the brightness level in the fixed quantity reaction may be the third level is pre-stored in a terminal.

Also, a reagent pad on an image of a biosensor obtained by the terminal may be discolored to red, a brightness level of the reagent pad may be a second level, and a brightness level of a region of reference brightness information, which corresponds to a fixed quantity reaction, may be a fourth level.

Because the reagent pad on the image of the biosensor is discolored to red, the terminal may determine that a positive reaction is obtained. Also, because the brightness level in the fixed quantity reaction is the third level whereas the brightness level of the region of the reference brightness information is the fourth level, the terminal may determine that measurement is performed in a dark environment. Thus, the terminal may change the image to be brighter. Accordingly, the brightness level of the region of the reference brightness information may be changed from the fourth level to the third level, and the brightness level of the reagent pad may be changed from the second level to the first level.

By using the changed brightness level of the reagent pad, the terminal may quantitatively measure biometric information. When a reagent pad is brighter, a corresponding numerical value is lower, and when the reagent pad is darker, the numerical value is higher. Because a brightness level of the reagent pad is a first level that is brighter than a brightness level, i.e., a third level, in a fixed quantity reaction, the terminal may determine that a numerical value corresponding to a reagent reaction is lower than a numerical value corresponding to the fixed quantity reaction. The terminal may display the detected numerical value as biometric information.

According to another exemplary embodiment, the terminal may compute quantitative biometric information using the obtained image without any calibration of the obtained image. For example, as illustrated on FIG. 26, the biosensor may include a reagent pad 2600 and reference brightness information 2601 through 2605 displayed around the reagent pad 2600. The terminal may compute the quantitative biometric information using an image obtained by capturing the reagent pad 2600 and the reference brightness information 2601 through 2605.

At least two pieces of reference information 2601 through 2605 may be displayed around the reagent pad 2600. For example, as illustrated on FIG. 26, five pieces of reference information 2601 through 2605 may be displayed. Each of the displayed pieces of the reference brightness information 2601 through 2605 may have a brightness different to each other. Referring to FIG. 26, each of the five pieces of the reference information 2601 through 2605 may have a brightness corresponding to one of five levels of brightness. A first reference brightness information 2601 may have a brightness corresponding to a first brightness level. A second reference brightness information 2602 may have a brightness corresponding to a second brightness level. A third reference brightness information 2603 may have a brightness corresponding to a third brightness level. A fourth reference brightness information 2604 may have a brightness corresponding to a fourth brightness level. A fifth reference brightness information 2605 may have a brightness corresponding to a fifth brightness level.

A color of the reagent pad 2600 may be changed as a result of a reagent reaction. The reagent pad 2600 may be discolored to blue of a variety of brightness level according to the reagent reaction. As illustrated on FIG. 26, the reagent pad 2600 may be discolored to blue of a brightness corresponding to the first brightness level among the five brightness levels. The brightness of the reagent pad 2600 may be identical to the brightness of the first reference brightness information 2601.

The terminal may obtain an image by capturing the reagent pad 2600 and the reference brightness information 2601 through 2605. A brightness of the image may differ according to an environment at the moment the image is captured. For example, if the image was captured in an environment that provides a sufficient lighting, the image may be brighter than an image captured in an environment that does not provide a sufficient lighting. Therefore, even if the reagent pad 2600 has an actual brightness corresponding to the first brightness level, a brightness of the reagent pad 2600 appeared in the obtained image may differ according to an environment.

The reference brightness information 2601 through 2605 may take the same effect of the lighting that the reagent pad 2600 takes. The reagent pad 2600 may take the same effect of the lighting that the first reference brightness information 2601 takes, wherein the first reference brightness information 2601 has the same brightness that the reagent pad 2600 has, Therefore, a brightness of the reagent pad 2600 appeared in the obtained image may be identical to a brightness of the first reference brightness information 2601 appeared in the image. In other words, if there exists a piece of reference brightness information 2601 through 2605 which has the same brightness that the reagent pad 2600 has, a brightness of the reagent pad 2600 appeared in the image may be identical to a brightness of the piece of reference brightness information 2601 through 2605 appeared in the image. Moreover, if there exists a piece of reference brightness information 2601 through 2605 which has a different brightness to a brightness of the reagent pad 2600, a brightness of the reagent pad 2600 appeared in the image may be different to a brightness of the piece of reference brightness information 2601 through 2605 appeared in the image.

Therefore, the terminal may compare the brightness of the reagent pad 2600 appeared in the image with the brightness of the reference brightness information 2601 through 2605 appeared in the image, without any calibration of the image. As a result of the comparison, the terminal may detect a piece from among the reference brightness information 2601 through 2605, wherein the piece has the same brightness as the reagent pad 2600 has. Referring to FIG. 26, the detected piece may be the first reference brightness information 2601.

The terminal may obtain an actual brightness of the reagent pad 2600 using the detected result. Referring to FIG. 26, the terminal may obtain information that an actual brightness of the reagent pad 2600 corresponds to the first brightness level. Consequently, the terminal may obtain an actual brightness of the reagent pad 2600 using information included in the image, regardless of an environment at the moment the image is captured.

The terminal may compute quantitative biometric information corresponding to the reagent reaction using the obtained actual brightness of the reagent pad 2600. For example, when the reagent pad 2600 is brighter, a corresponding numerical value may be lower, and when the reagent pad 2600 is darker, the corresponding numerical value may be higher. Further, a brightness corresponding to the fixed quantity reaction may be the third brightness level. Referring to FIG. 26, the terminal may determine that a numerical value corresponding to the reagent reaction is lower than a numerical value corresponding to the fixed quantity reaction, since the actual brightness of the reagent pad 2600 turns out to be the first brightness level. The terminal may display the detected numerical value as the biometric information.

Figure 29:
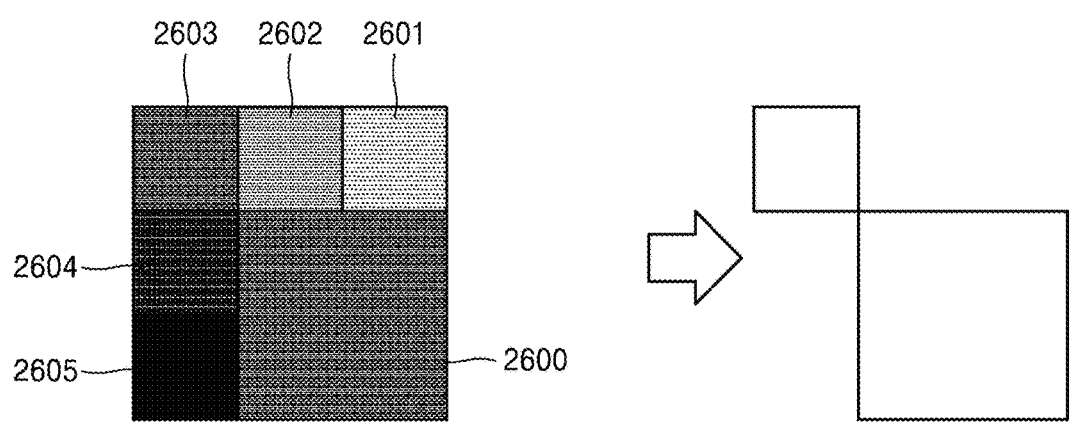
FIG. 29 is another reference diagram for describing a process of detecting an actual brightness of a reagent pad, according to an exemplary embodiment.
Figure 30:
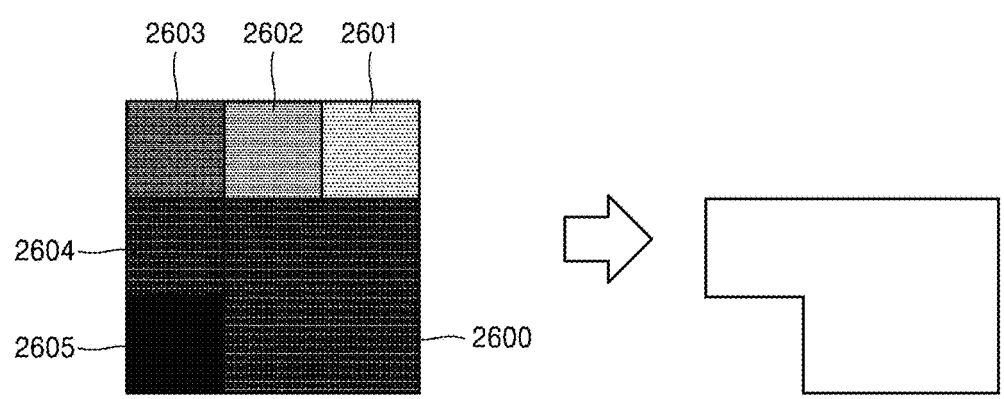
FIG. 30 is another reference diagram for describing a process of detecting an actual brightness of a reagent pad, according to an exemplary embodiment.
Figure 31:
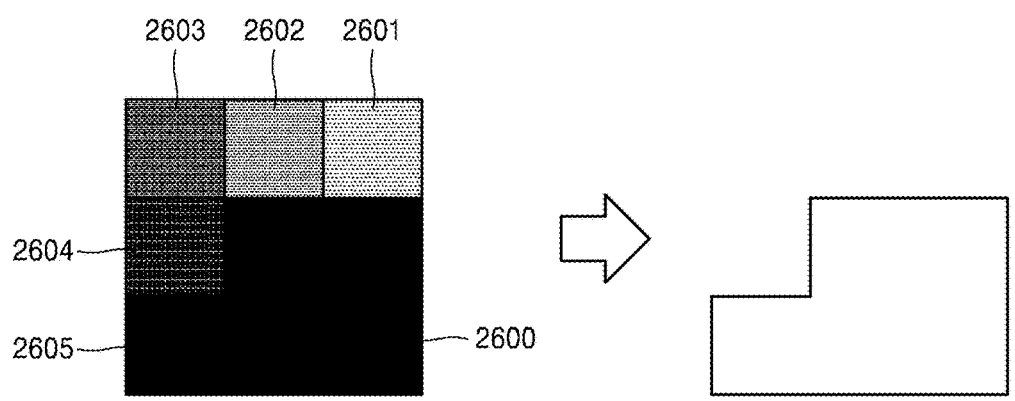
FIG. 31 is another reference diagram for describing a process of detecting an actual brightness of a reagent pad, according to an exemplary embodiment.

FIG. 27 through FIG. 31 are reference diagrams for describing a process of detecting an actual brightness of a reagent pad. Referring to FIG. 31, a biosensor may include a reagent pad 2600 and five pieces of reference information 2601 through 2605 displayed around the reagent pad 2600. The terminal may obtain an image by capturing the biosensor.

The terminal may process the obtained image. The terminal may process the image using brightness information of pixels included in the image. The terminal may detect a region including pixels which have the same brightness as a brightness of a part corresponding to the reagent pad 2600 in the image.

The terminal may recognize a shape of the detected region. Even though a brightness of the reagent pad 2600 may differ according to a reagent reaction, brightnesses of the reference brightness information 2601 through 2605 may be constant regardless of the reagent reaction. Therefore, a shape of the detected region may differ according to the reagent reaction.

For example, an actual brightness of the reagent pad 2600 may be the first brightness level according to the reagent reaction. The terminal may obtain the image illustrated on the left on FIG. 27 by capturing the biosensor. The terminal may detect the shape illustrated on the right on FIG. 27 by processing the obtained image.

As another example, an actual brightness of the reagent pad 2600 may be the second brightness level according to the reagent reaction. The terminal may obtain the image illustrated on the left on FIG. 28 by capturing the biosensor. The terminal may detect the shape illustrated on the right on FIG. 28 by processing the obtained image.

As another example, an actual brightness of the reagent pad 2600 may be the third brightness level according to the reagent reaction. The terminal may obtain the image illustrated on the left on FIG. 29 by capturing the biosensor. The terminal may detect the shape illustrated on the right on FIG. 29 by processing the obtained image.

As another example, an actual brightness of the reagent pad 2600 may be the fourth brightness level according to the reagent reaction. The terminal may obtain the image illustrated on the left on FIG. 30 by capturing the biosensor. The terminal may detect the shape illustrated on the right on FIG. 30 by processing the obtained image.

As another example, an actual brightness of the reagent pad 2600 may be the fifth brightness level according to the reagent reaction. The terminal may obtain the image illustrated on the left on FIG. 31 by capturing the biosensor. The terminal may detect the shape illustrated on the right on FIG. 31 by processing the obtained image.

Figure 27:
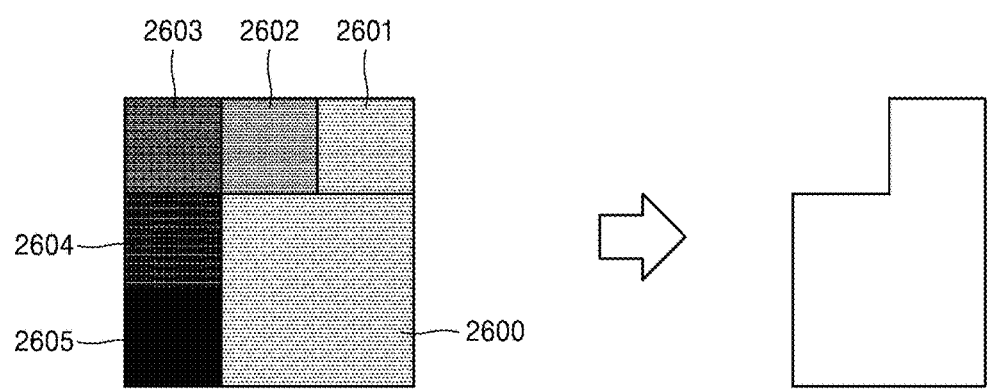
FIG. 27 is a reference diagram for describing a process of detecting an actual brightness of a reagent pad, according to an exemplary embodiment.
Figure 28:
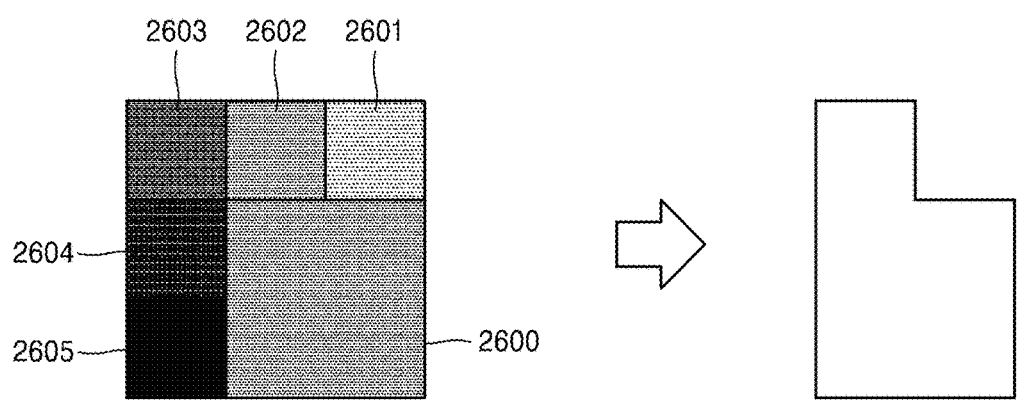
FIG. 28 is another reference diagram for describing a process of detecting an actual brightness of a reagent pad, according to an exemplary embodiment.

The terminal may detect an actual brightness of the reagent pad 2600 based on the recognized shape of the detected region. For example, when the shape illustrated on the right on FIG. 27 is recognized, the terminal may determine that an actual brightness of the reagent pad 2600 is the first brightness level. When the shape illustrated on the right on FIG. 28 is recognized, the terminal may determine that an actual brightness of the reagent pad 2600 is the second brightness level. When the shape illustrated on the right on FIG. 29 is recognized, the terminal may determine that an actual brightness of the reagent pad 2600 is the third brightness level. When the shape illustrated on the right on FIG. 30 is recognized, the terminal may determine that an actual brightness of the reagent pad 2600 is the fourth brightness level. When the shape illustrated on the right on FIG. 31 is recognized, the terminal may determine that an actual brightness of the reagent pad 2600 is the fifth brightness level.

Figure 32:
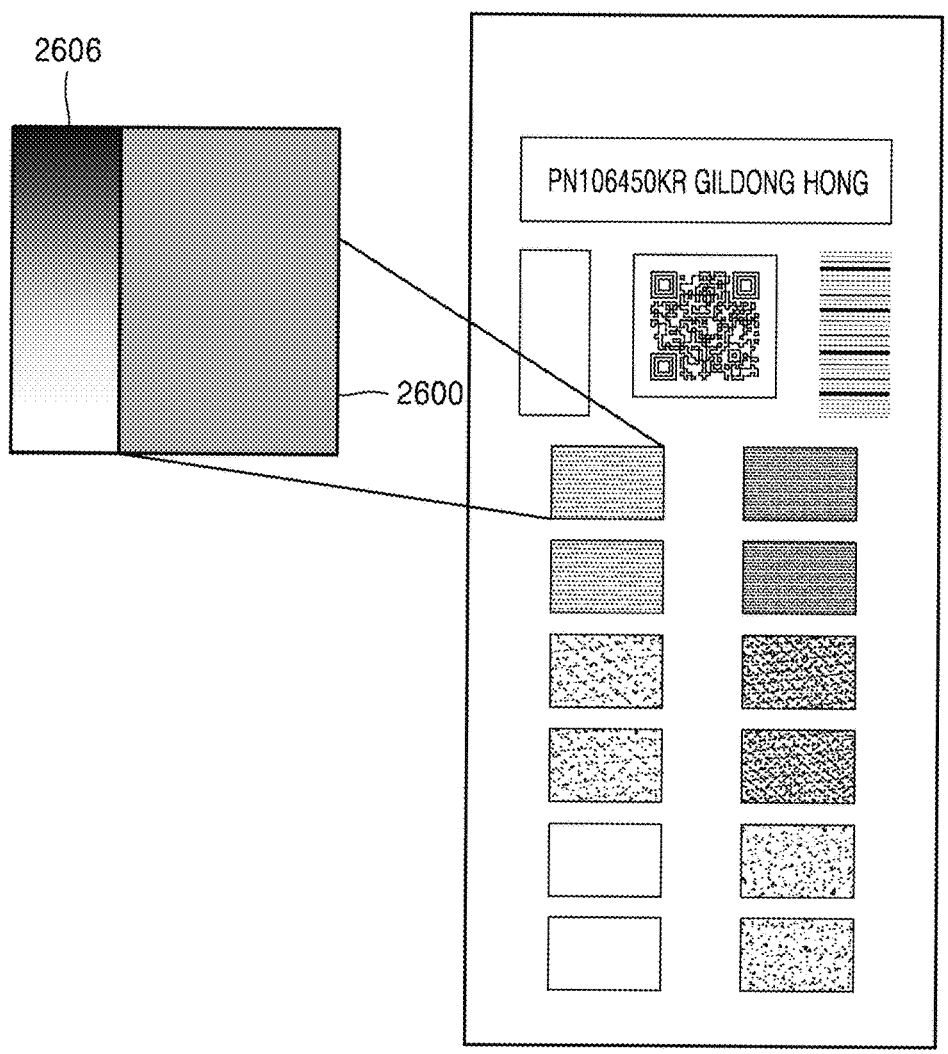
FIG. 32 is another view illustrating a biosensor displaying reference brightness information around a reagent pad, according to an exemplary embodiment.

FIG. 32 is another view illustrating a biosensor displaying reference brightness information around a reagent pad. Referring to FIG. 32, reference brightness information 2606 may be displayed continuously, whereas reference brightness information 2601 through 2605 is displayed discretely on FIG. 26. For example, as illustrated on FIG. 32, the reference brightness information 2606 may be displayed continuously in an upward direction, from the first brightness level to the fifth brightness level. In other words, the reference brightness information 2606 may be displayed continuously in an upward direction, from a brightness corresponding to the maximum reaction to a brightness corresponding to the minimum reaction or non-reaction. For example, the reference brightness information 2606 may be displayed continuously from a brightness corresponding to a reaction rate of zero percent to a brightness corresponding to a reaction rate of one hundred percent, wherein the reaction rate of zero percent corresponds to the minimum reaction or non-reaction, and the reaction rate of one hundred percent corresponds to the maximum reaction.

The terminal may obtain an image by capturing the reagent pad 2600 and the reference brightness information 2606. The terminal may compare a brightness of a part corresponding to the reagent pad 2600 in the image with a brightness of a part corresponding to the reference brightness information 2606. The terminal may detect a location of a part having the same brightness as the brightness of the reagent pad 2600, in the reference brightness information 2606. For example, an actual brightness of the reagent pad 2600 may be the third brightness level. The terminal may determine that a part having the same brightness as the brightness of the reagent pad 2600 is located in the middle of the reference brightness information 2606.

As another example, an actual reaction rate of the reagent reaction may be fifty-six percent, wherein a reaction rate of zero percent corresponds to the minimum reaction or non-reaction, and a reaction rate of one hundred percent corresponds to the maximum reaction. The terminal may determine that a part having the same brightness as the brightness of the reagent pad 2600 is located at a fifty-six-percent point within the full length of the reference brightness information 2606. The terminal may determine that an actual reaction rate of the reagent reaction is fifty-six percent, based on the detected location.

The terminal may detect an actual brightness of the reagent pad 2600 based on the detected location. For example, when it is determined that a part having the same brightness as the brightness of the reagent pad 2600 is located in the middle of the reference brightness information 2606, the terminal may determine that an actual brightness of the reagent pad 2600 is the third brightness level. As another example, when it is determined that a part having the same brightness as the brightness of the reagent pad 2600 is located at a fifty-six-percent point within the full length of the reference brightness information 2606, the terminal may determine that an actual brightness of the reagent pad 2600 corresponds to a reaction rate of fifty-six percent.

Figure 33:
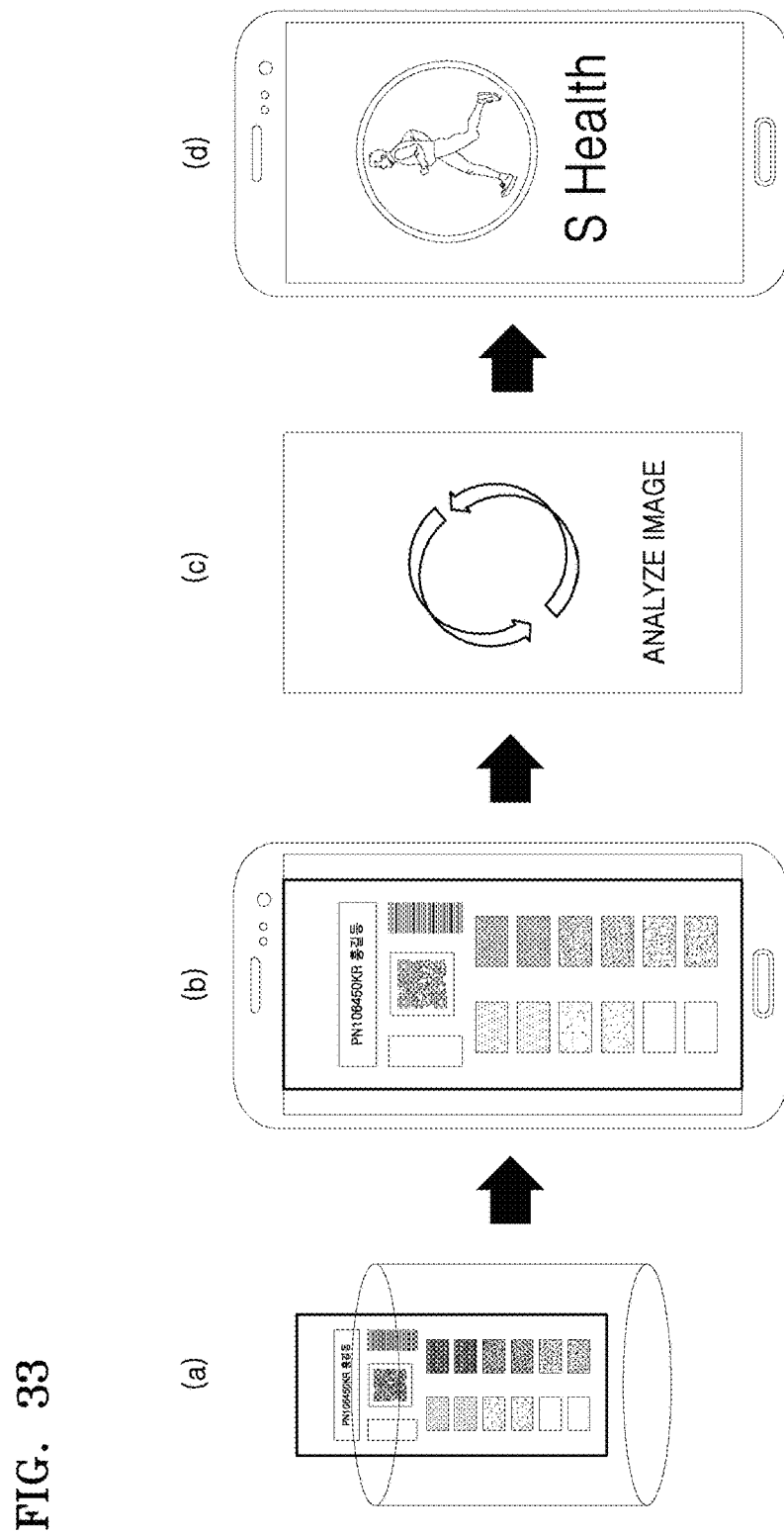
FIG. 33 is a diagram for describing an entire operation of executing, by a terminal, a sample measuring program, according to an exemplary embodiment.

FIG. 33 is a diagram for describing an entire operation of executing, by a terminal, a sample measuring program, according to an exemplary embodiment.

Referring to FIG. 33 portion (a) of FIG. 33, a user of the terminal may input his/her sample to a biosensor.

Referring to FIG. 33 portion (b) of FIG. 33, the user may obtain an image of the biosensor by using an input interface (a camera) of the terminal.

Referring to FIG. 33 portion (c) of FIG. 33, the terminal may analyze the image and derive a relative difference of brightness of a reagent pad based on brightness in a fixed quantity reaction as a quantitative value based on whether the reagent pad is discolored, the brightness of the reagent pad, and reference brightness information.

Referring to FIG. 33 portion (d) of FIG. 33, the terminal displays detected biometric information to provide the detected biometric information to the user.

Figure 34:
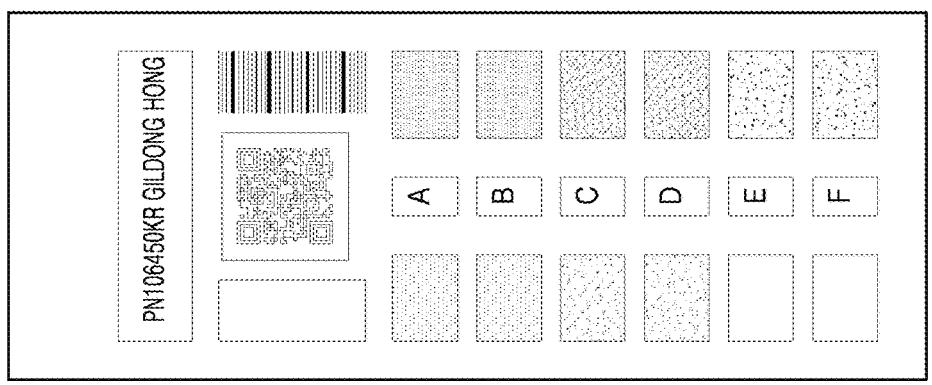
FIG. 34 is a diagram illustrating a biosensor displaying reference color information, according to an exemplary embodiment.
Figure 34:
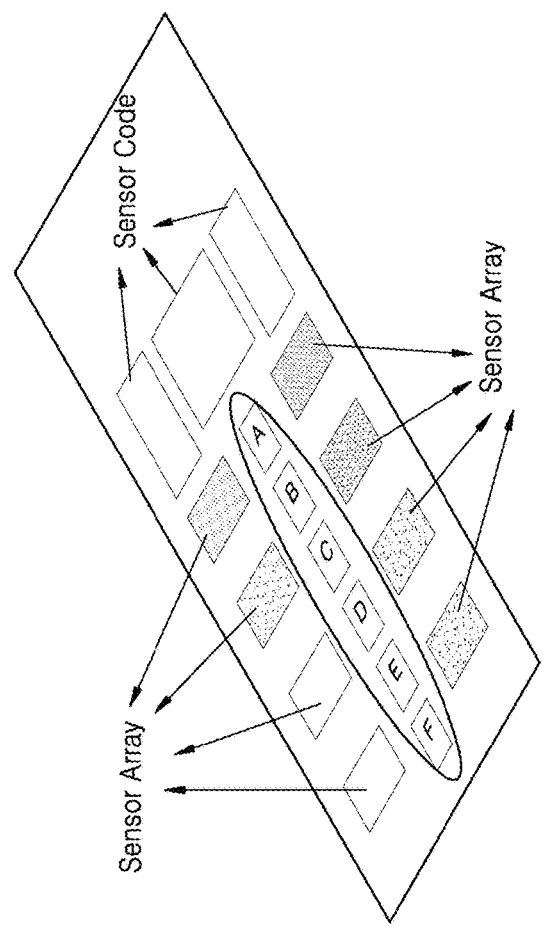

FIG. 34 is a diagram illustrating a biosensor displaying reference color information, according to an exemplary embodiment.

When the biosensor includes a plurality of reagent pads, the reagent pads may be discolored to different colors, but it may be difficult to classify the discolored colors. Accordingly, reference color information A through F is displayed on the biosensor as a reference color display region to obtain accurate discoloration information.

A color of a reagent pad, which is obtained when a reagent reaction is positive, may be displayed on a biosensor as a reference color. For example, when a ketone body reagent reaction is positive, a reagent pad may be discolored to dark purple. Thus, dark purple may be displayed on a biosensor as reference color information to support accurate measurement of biometric information.

Figure 35:
FIG. 35 is a diagram for describing a method of analyzing biometric information by using an exhaled breath, according to an exemplary embodiment.

FIG. 35 is a diagram for describing a method of analyzing biometric information by using an exhaled breath, according to an exemplary embodiment.

As described above, a sample including biometric information may be urine, sweat, a tear, saliva, or blood, and in addition, may be gas, such as an exhaled breath.

As shown in FIG. 35, a user may breathe out into a biosensor capable of measuring an exhaled breath. Here, the biosensor may be an electronic device, such as a breathalyzer, or may be a gas tube including a dye.

The biosensor may include a dye, and may measure biometric information as the dye reacts with an exhaled breath and a color of the dye changes. Such a bio-sensing technology is referred to as a colorimetric sensor array technology, and a pattern of a color change may be determined by arranging a plurality of dyes, which change color, on a 2-dimensional (2D) plane.

Figure 36:
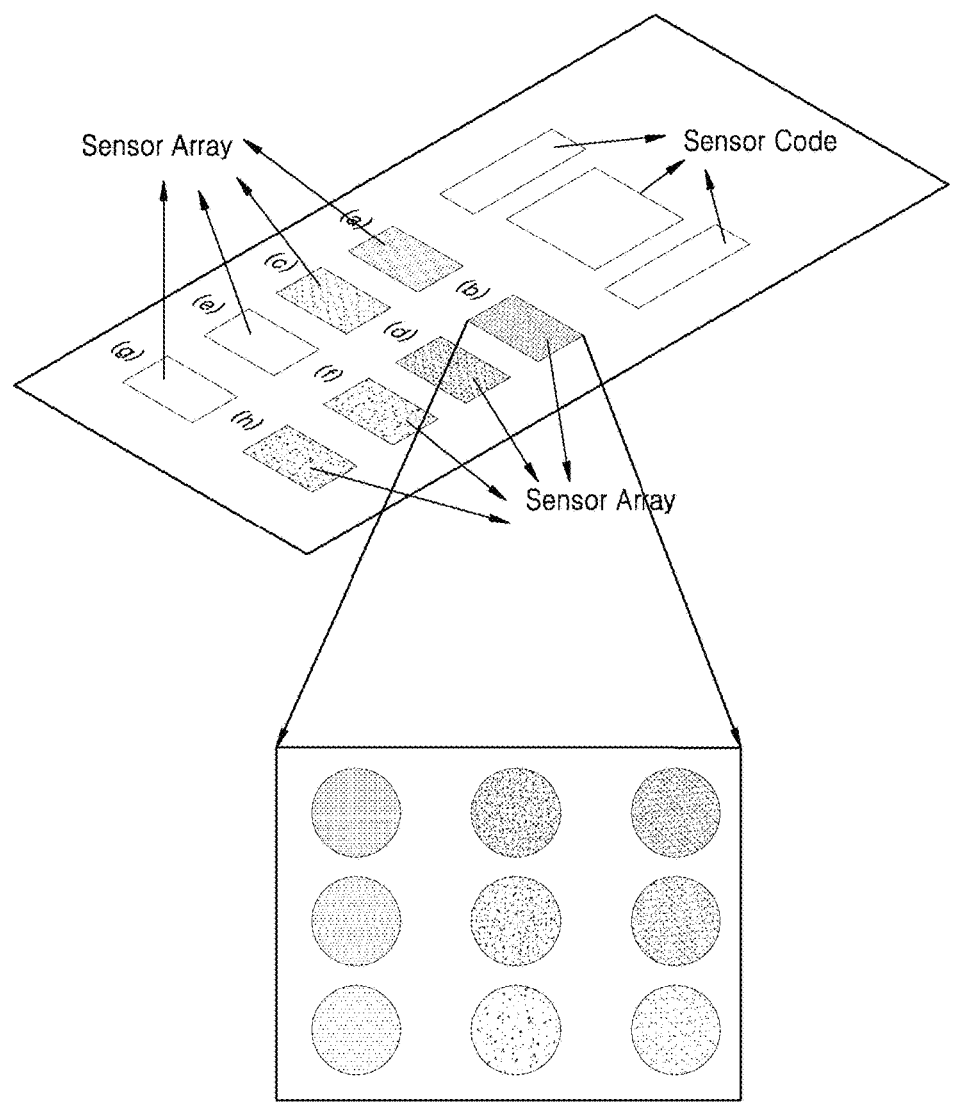
FIG. 36 is a diagram illustrating an example of a biosensor measuring an exhaled breath, according to an exemplary embodiment.

FIG. 36 is a diagram illustrating an example of a biosensor measuring an exhaled breath, according to an exemplary embodiment.

As shown in FIG. 36, a tube containing an amount of gas may be used as a device for measuring an exhaled breath. In the tube, a plurality of dyes is arranged on a 2D plane, and biometric information may be measured by using a result of discoloration of the plurality of dyes according to reactions with an exhaled breath.

The plurality of dyes may be used to diagnose different diseases. For example, a dye on a reagent pad (a) may be used to diagnose asthma, a dye on a reagent pad (b) may be used to diagnose a bad breath, and a dye on a reagent pad (c) may be used to diagnose a chronic obstructive pulmonary disease. A plurality of reagent pads may respectively include a plurality of dyes to respectively diagnose a plurality of diseases, or a combination of the plurality of reagent pads may be used to diagnose one disease.

For example, a cancer may be diagnosed through an exhaled breath. Metabolism materials of cancer cells may be dissolved in blood, and may be externally discharged through the exhaled breath. Materials discharged through the exhaled breath may react with a plurality of dyes arranged on a tube, and the metabolism materials of the cancer cells may be detected based on whether colors of the dyes are changed.

As shown in FIG. 36, referring to reagent pads (a) through (h), a plurality of dyes are arranged on the tube, i.e., the biosensor, in 2 dimensions, wherein the dyes have intrinsic colors. After the dyes are discolored by reacting with materials in an exhaled breath, a user may capture an image of the tube by using an optical image sensor (a camera) of a terminal.

A plurality of dyes included in a reagent pad may be distinguished from each other by colors and brightness thereof. For example, dyes included in the reagent pad (b) may be distinguished into three groups of red, yellow, and blue dyes, each having different brightness.

The terminal may obtain the image of the tube and may also obtain discoloration information of the reagent pads, reference brightness information, and ID information from the obtained image. The reference brightness information may be displayed around the dye or at a location separate from the reagent pad. Because the reference brightness information has been described above with reference to FIGS. 10 through 13, details thereof are not provided again.

The terminal may determine brightness of a reagent pad including a dye, and may pre-store, in the storage, brightness information in fixed quantity reactions between dyes and materials in an exhaled breath. Thus, the terminal may derive a quantitative value corresponding to a reagent reaction by referring to a reagent pad having high similarity in a color and brightness as the reagent reaction from the received image. The terminal may derive the quantitative value corresponding to the reagent reaction by searching an internal DB or an external DB for information about brightness information of a dye and reference brightness information that is the same or similar to the brightness information of the dye.

A biosensor used to analyze an exhaled breath may include a plurality of reagent pads respectively including a plurality of dyes in 2 dimensions, wherein arrangement information of the reagent pads may be used as ID information of the biosensor. The dyes have intrinsic colors, and patterns of the colors may be stored in a DB to be used as ID information of a user or the biosensor. For example, when the biosensor includes eight reagent pads, locations of the reagent pads may be combined to show one pattern. The terminal may obtain information about a patient who is using the biosensor or the ID information of the biosensor based on the pattern on an image of the biosensor.

Figure 37:
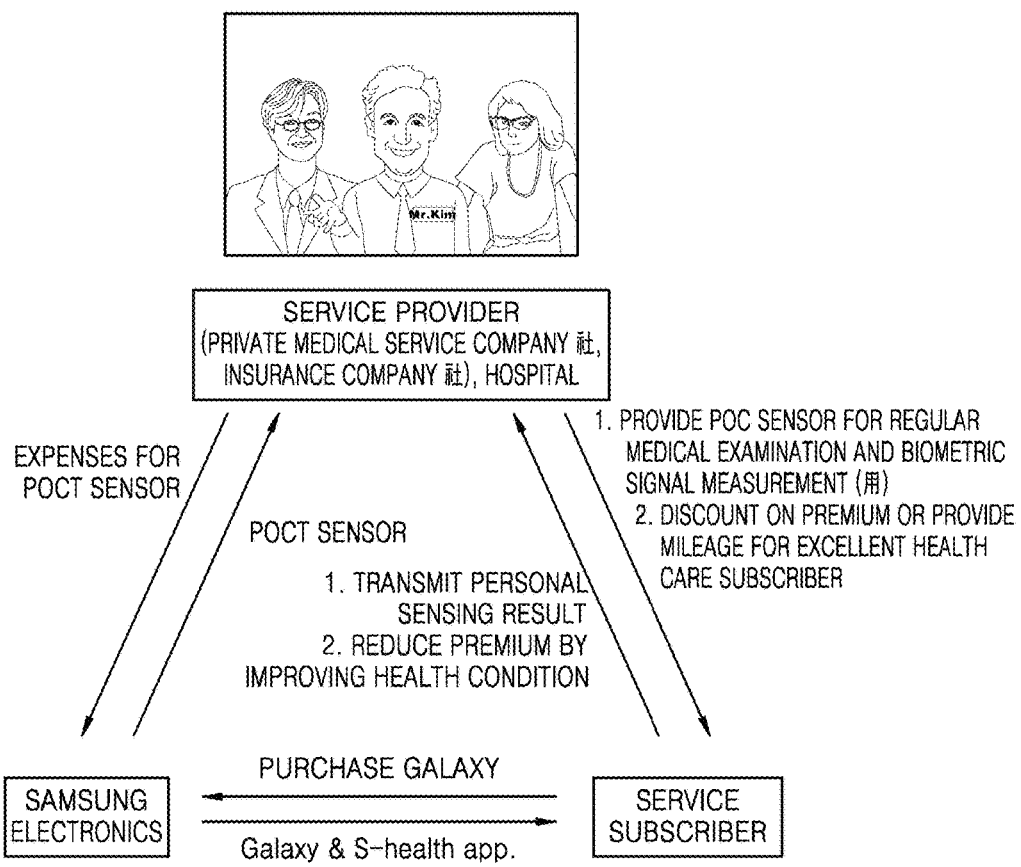
FIG. 37 is a diagram illustrating a medical system providing a measuring service to a sample measuring terminal, according to an exemplary embodiment.

FIG. 37 is a diagram illustrating a medical system providing a measuring service to a sample measuring terminal, according to an exemplary embodiment.

Quantitative value calibration and biometric information measurement through a reagent reaction described above with reference to FIGS. 1 through 28 may be configured as a medical service between a manufacturer of a terminal (e.g., Samsung Electronics), a medical service provider, and a user of the terminal (e.g., a service subscriber).

A manufacturer of a terminal may manufacture a terminal capable of measuring biometric information from a biosensor through an optical image sensor. Also, the manufacturer may manufacture a biosensor capable of performing point-of-care diagnostics (POCT).

A service provider may be an institution that uses biometric information, such as a medical institution, for example, a hospital or a pharmacy, or an insurance company. The service provider has a network system, such as a server, to communicate with a terminal, and may store a DB of various types of information, such as results of reagent reactions. The service provider may also manufacture a biosensor capable of performing POCT.

A user of a terminal receives a medical service, and may collect his/her sample, such as urine or blood, to measure biometric information by using an application, such as S-health, installed in the terminal. The user may make a contract (subscription contract) with a service provider offline or online. For example, the user may be a patient and the service provider may be a hospital where the user was hospitalized. If the user has difficulties in going to the hospital or has to measure biometric information, the user may measure the biometric information by using the terminal. Thus, the hospital, i.e., the service provider, may provide a biosensor capable of performing POCT to the user. As another example, the user may be a person who wants to take up an insurance policy and the service provider may be an insurance company. Because the user may measure and transmit his/her biometric information to take up the insurance company, the service provider may provide a biosensor capable of performing POCT to the user.

The user may measure the biometric information by using an application installed in the terminal and transmit the biometric information to the service provider, and the service provider may store the biometric information of the user. The service provider and the terminal may store the biometric information of the user to share information about treatments for various diseases.

The service provider may provide a medical service to the user periodically or aperiodically to manage a health condition of the user. A service of managing the health condition of the user in real-time, together with biometric information measured by a wearable device, such as a smart watch or smart glasses, may be provided to the user.

Figure 38:
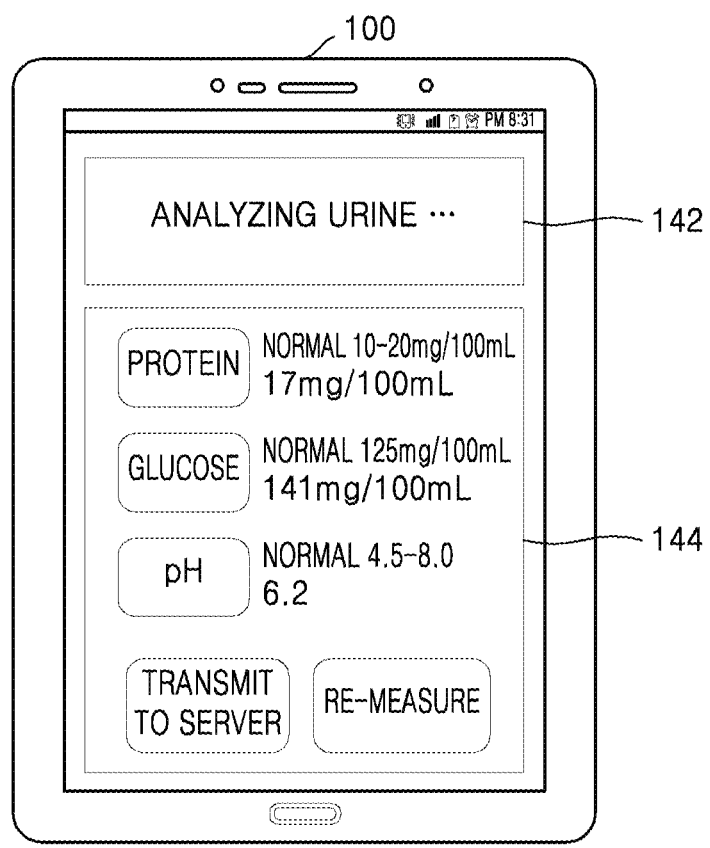
FIG. 38 is a view illustrating a screen of a terminal, in which a sample measuring program is executed, according to an exemplary embodiment.

FIG. 38 is a view illustrating a screen of the terminal 100, in which a sample measuring program is executed, according to an exemplary embodiment.

A user of the terminal 100 may input his/her urine sample to a sample inlet of a biosensor, and obtain an image of the biosensor including a result of a reagent reaction by using the terminal 100.

The terminal 100 may analyze the image to perform quantitative measurement and qualitative measurement based on a discoloration result, a color, and brightness of the reagent reaction, and reference brightness information.

A display of the terminal 100 includes display regions 142 and 144. The display region 142 may display information that the urine sample is being analyzed in text, such as "analyzing urine", or in an image.

The display region 144 may display biometric information obtained by analyzing the urine sample, and may receive an input from the user. For example, the terminal 100 may display a normal range and a measured value of protein as a result of analyzing the urine sample, and the user may touch a protein button to manipulate the terminal 100 to display brief information about protein diagnosis. Alternatively, when the protein button is touched, another piece of biometric information may be displayed.

The terminal 100 may display a button for transmitting the biometric information to an external device and a button for re-measuring biometric information if the biometric information is abnormal. The biometric information may be determined to be abnormal when a temperature of the urine sample is outside a range of an adequate temperature, when an expiration date of the biosensor is passed, or when a numerical value of the biometric information is outside a normal range.

In relation to the medical system described above with reference to FIG. 37, the terminal 100 may provide a screen enabling the user to communicate with a doctor, i.e., the service provider, via remote video communication. When the terminal 100 stores information about the numerical value of the biometric information, the stored information may be provided to the user. For example, when the terminal 100 stores information about a recommended food and a prohibited food regarding diabetes, and the numerical value of the biometric information indicates that the user has diabetes, the terminal 100 may display the information about the recommended food and the prohibited food.

Figure 39:
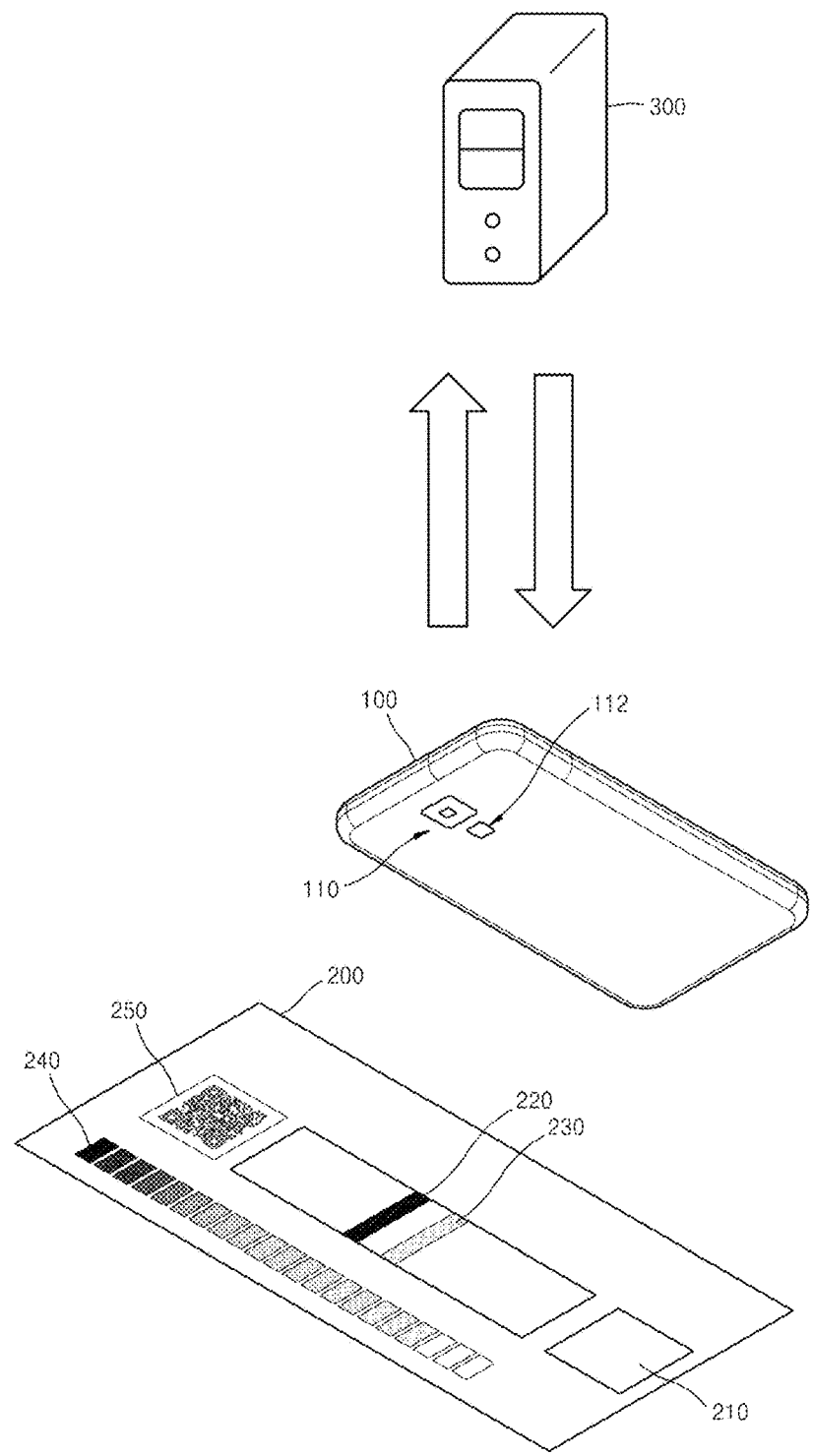
FIG. 39 is a network diagram illustrating a network environment on which a terminal operates, according to an exemplary embodiment.

FIG. 39 is a network diagram illustrating a network environment on which a terminal operates. Referring to FIG. 39, the terminal 100 may be connected to a server 300 via a communication network. The terminal 100 may obtain an image by capturing a biosensor 200. The terminal 100 may transmit the obtained image to the server 300. The terminal 100 may receive an analysis result with respect to the image from the server 300. The terminal 100 may display the received analysis result. A more detailed description about operations of the terminal 100 and the server 300 would be described hereafter with reference to FIG. 40.

Figure 40:
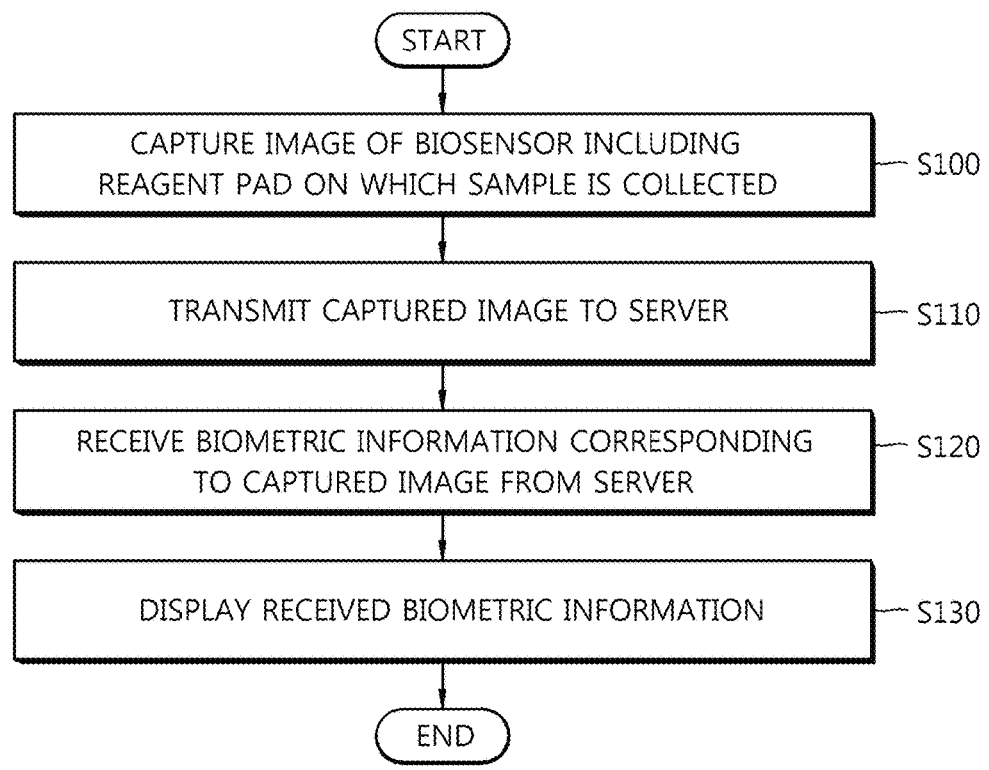
FIG. 40 is a flowchart of a process of displaying biometric information using an image of a biosensor, according to an exemplary embodiment.

FIG. 40 is a flowchart of a process of displaying biometric information using an image of a biosensor. Referring to FIG. 40, in operation S100, an image of a biosensor including a reagent pad on which a sample is collected may be captured. The terminal 100 may capture the image of the biosensor 200 through a camera included in the terminal 100. The terminal 100 may obtain the image by capturing the reagent pad 2600 and reference brightness information 2601 through 2605 included in the biosensor 200.

In operation S110, the captured image may be transmitted to a server 300. The terminal 100 may transmit the obtained image to the server. The server 300 may receive the image. The server 300 may process and analyze the image. The server 300 may detect information about a color and a brightness of a part corresponding to the reagent pad 2600 in the image. Further, the server 300 may detect information about colors and brightnesses of a part corresponding to the reference brightness information 2601 through 2605. The server 300 may compare the information about the part corresponding to the reagent pad 2600 with the information of the part corresponding to the reference brightness information 2601 through 2605. The server 300 may compute quantitative biometric information corresponding to a reagent reaction using a result of the comparison.

In operation 120, biometric information corresponding to the image may be received from the server 300. The terminal 100 may receive an analysis result of the image from the server 300. The terminal 100 may receive quantitative biometric information corresponding to a reagent reaction as the analysis result from the server 300.

Figure 41:
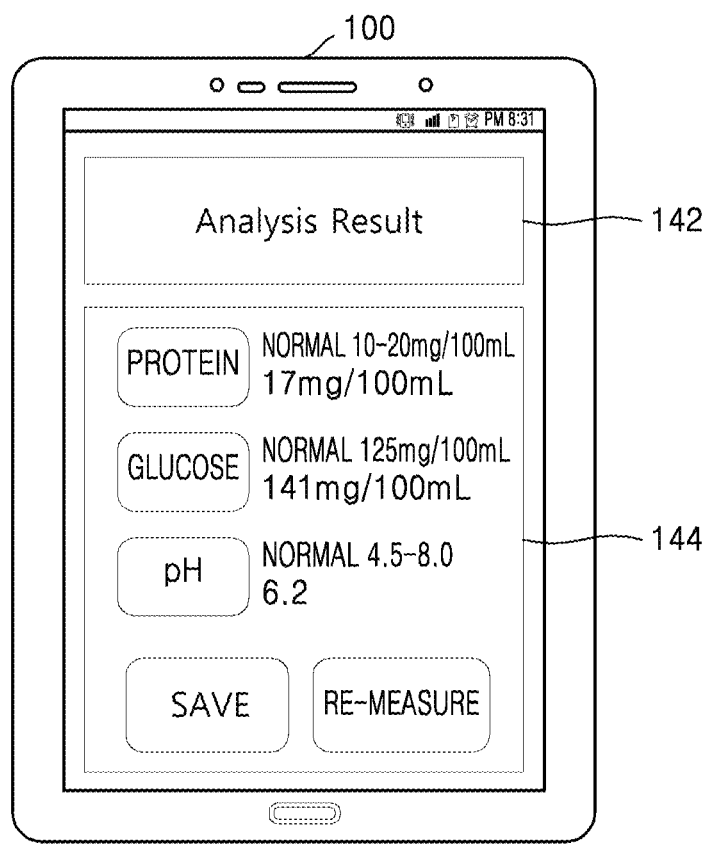
FIG. 41 is a screen showing an analysis result displayed on a terminal, according to an exemplary embodiment.

In operation S130, the received biometric information may be displayed. The terminal 100 may display the received analysis result. The terminal 100 may display the quantitative biometric information included in the analysis result using a display of the terminal 100. FIG. 41 is a screen showing the analysis result displayed on the terminal 100.

Figure 42:
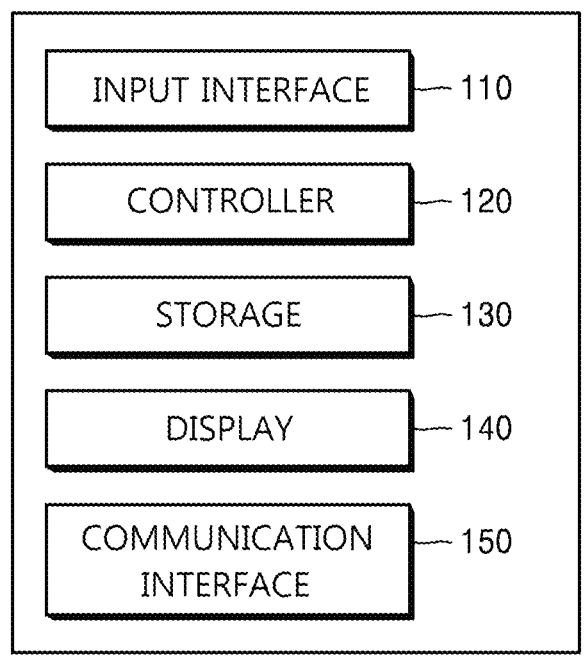
FIG. 42 is a block diagram of a structure of a terminal, according to an exemplary embodiment.

FIG. 42 is a block diagram of a structure of the terminal 100, according to an exemplary embodiment.

The terminal 100 according to an exemplary embodiment includes the input interface 110 that receives data from an external source, a controller 120 that processes the data, and a storage 130 that stores the input or processed data The terminal 100 further includes a display 140 that displays the data on a screen of the terminal 100, and a communication interface 150 that communicates with another device. According to an exemplary embodiment, the terminal 100 may be a smart phone that includes an operating system (OS), and accesses the Internet or executes various programs. The smart phone may be a digital mobile device on which an OS and a communication function are mounted such that various types of content are conveniently used in a user environment (UI/UX). According to an exemplary embodiment, the terminal 100 may be a multimedia player or a personal computer (PC).

The input interface 110 is an interface that receives data, such as content, displayed on the display 140, and may include at least one of a universal serial bus (USB), a parallel advanced technology attachment (PATA), a serial advanced technology attachment (SATA), a flash media, the Ethernet, Wi-Fi, and Bluetooth. As occasion demands, the terminal 100 may include an information storage device, such as an optical disk drive or a hard disk, and receive the data through the information storage device.

Also, the terminal 100 according to an exemplary embodiment may include a camera including an optical image sensor as the input interface 110. An image received through a camera module may be processed as one piece of data.

The input interface 110 may further include a sensor for measuring a temperature or humidity, in addition to the camera. Here, the input interface 110 may not only include a temperature sensor that measures an internal temperature of the terminal 100, but may also include a temperature sensor that measures an external temperature of the terminal 100. Also, a humidity sensor that measures humidity may also correspond to the input interface 110 according to an exemplary embodiment.

The input interface 110 may be a touch screen in which a touch panel and an image panel form a layer structure. The touch panel may be a capacitance type touch panel, a resistance film type touch panel, or an infrared type touch panel. The image panel may be a liquid crystal panel or an organic light-emitting panel. Because the touch panel is a well-known technology, details thereof are not provided herein. The image panel may display graphic of a user interface.

The controller 120 encodes or decodes the data input to the input interface 110.

The controller 120 provides a user interface based on an OS of the terminal 100. The user interface may reflect a usage of the user.

The storage 130 may store the data input to or processed by the terminal 100. According to an exemplary embodiment, because biometric information is determined by analyzing an image of a biosensor, the storage 130 may store, as a DB, various types of information related to measurement of biometric information, such as information about various reagent reactions, ID information of biosensors, and reference brightness information of reagent pads.

The display 140 may display the data processed by the terminal 100 under a user interface environment. According to an exemplary embodiment, because the image of the biosensor is obtained and analyzed, the display 140 may display the image of the biosensor, which is obtained by the camera, and may display results of analyzing a reagent reaction as shown in FIG. 38. In addition, the display 140 may display information guiding the user to input at least one of various manipulation commands.

The communication interface 150 may transmit and receive data and a control command to and from another device. The communication interface 150 may use a well-known communication module, such as an infrared communication module, a radio communication module, or an optical communication module. For example, the communication interface 150 may use an infrared communication module that satisfies an infrared data association (IrDA) protocol. As another example, a communication module using 2.4 GHz frequency or a communication module using a Bluetooth may be used as the communication interface 150.

The communication interface 150 according to an exemplary embodiment may request a server of a service provider, such as a hospital, a pharmacy, or an insurance company, for data, and may receive the data transmitted from the server.

While not restricted thereto, an exemplary embodiment can be embodied as computer-readable code on a computer-readable recording medium. For example, a control program that controls the above-described operations may be embodied as computer-readable code on a computer-readable recording medium. The computer-readable recording medium is any data storage device that can store data that can be thereafter read by a computer system. Examples of the computer-readable recording medium include read-only memory (ROM), random-access memory (RAM), CD-ROMs, magnetic tapes, floppy disks, and optical data storage devices. The computer-readable recording medium can also be distributed over network-coupled computer systems so that the computer-readable code is stored and executed in a distributed fashion. Also, an exemplary embodiment may be written as a computer program transmitted over a computer-readable transmission medium, such as a carrier wave, and received and implemented in general-use or special-purpose digital computers that execute the programs. Moreover, it is understood that in exemplary embodiments, one or more units can include circuitry, a processor, a microprocessor, etc., and may execute a computer program stored in a computer-readable medium.

The foregoing exemplary embodiments and advantages are examples and are not to be construed as limiting. The present teaching can be readily applied to other types of apparatuses. Also, the description of exemplary embodiments is intended to be illustrative, and not to limit the scope of the claims, and many alternatives, modifications, and variations will be apparent to those skilled in the art.

What is claimed is:

1. A method of a terminal measuring biometric information, the method comprising:
receiving an image of a biosensor comprising a reaction region including a reagent that reacts with a sample, and comprising reference brightness information configured to display and indicate different discrete brightnesses with respect to a same color; and
determining a degree of a reaction by comparing a brightness of the reaction region in the received image with the reference brightness information in the received image,
wherein the determining the degree of the reaction comprises:
detecting a region in the received image, the region including pixels having a same brightness as a brightness of a part corresponding to the reaction region in the received image, and the region including a portion of the reaction region and a portion of the reference brightness information, in the received image;
recognizing a shape of the detected region;
determining an actual brightness of the reaction region, based on the recognized shape; and
determining the degree of the reaction corresponding to the determined actual brightness.

2. The method of claim 1, further comprising:
determining the brightness of the reaction region in the received image; and
determining the reference brightness information in the received image.

3. The method of claim 1, further comprising determining a result of the reaction, based on the degree of the reaction.

4. The method of claim 1, further comprising:
acquiring identification (ID) information of the biosensor from the received image; and
determining the degree of the reaction, based on the ID information of the biosensor.

5. The method of claim 4, wherein the ID information comprises at least one among a quick response code, a barcode, an image, and text.

6. The method of claim 4, further comprising:
determining whether an expiration date of the biosensor has passed, the expiration date being included in the ID information; and
displaying at least one among unserviceability of the biosensor and invalidity of the reaction, in response to the determining that the expiration date has passed.

7. The method of claim 1, further comprising:
acquiring temperature information that is indicated by a temperature measurer included in the biosensor, from the received image; and
determining a temperature of the sample, based on the temperature information.

8. The method of claim 7, wherein the determining the degree of the reaction comprises:
determining the degree of the reaction, based on the determined temperature of the sample and temperature information of a reaction of the sample.

9. The method of claim 7, wherein the temperature measurer is configured to be attached to at least one among a sample inlet of a reagent pad of the biosensor and the reaction region of the reagent pad.

10. The method of claim 7, further comprising:
determining whether the temperature of the sample is equal to or higher than a pre-set temperature; and
displaying a message indicating impossibility of measuring the sample.

11. The method of claim 7, further comprising:
determining whether the temperature of the sample is lower than or equal to a pre-set temperature; and
displaying a message indicating impossibility of measuring the sample.

12. The method of claim 7, wherein the temperature measurer is displayed on a reagent pad of the biosensor in at least one among a linear shape, a radial shape, and a circular shape.

13. The method of claim 1, further comprising measuring a room temperature, using a temperature sensor that is included in the terminal.

14. The method of claim 1, further comprising determining a room temperature that is indicated by a temperature sensor that is attached to the biosensor in the received image.

15. The method of claim 1, wherein the determining the degree of the reaction comprises:
detecting a first brightness information among the reference brightness information, the first brightness information corresponding to the brightness of the reaction region; and
determining the degree of the reaction corresponding to the first brightness information.

16. The method of claim 1, wherein the reference brightness information indicates different continuous brightnesses with respect to the same color,
wherein the different continuous brightnesses are disposed continuously within the reference brightness information, and
wherein the determining the degree of the reaction comprises:
detecting a first brightness information among the reference brightness information, the first brightness information corresponding to the brightness of the reaction region;
detecting a location in which the first brightness information is located within the reference brightness information; and
determining the degree of the reaction corresponding to the detected location.

17. The method of claim 1, wherein the degree of the reaction is determined based on a degree of the reaction in a database that is stored in a storage of the terminal.

18. The method of claim 1, wherein the biosensor comprises a reagent pad including a control line having a color changing according to the reagent reaction.

19. The method of claim 1, wherein the biosensor comprises reagent pads supporting reactions between the reagent and the sample, and
wherein an identification information of the biosensor is acquired based on locations of the reagent pads in the received image.

20. The method of claim 1, wherein the biosensor is set configured to analyze at least one among urine, blood, sweat, a tear, saliva, and an exhaled breath.

21. A terminal for measuring biometric information, the terminal comprising:
- an input interface configured to receive an image of a biosensor including a reaction region that reacts with a sample, and including reference brightness information configured to display and indicate different discrete brightnesses with respect to a same color; and
- a controller configured to determine a degree of a reaction by comparing a brightness of the reaction region in the received image with the reference brightness information in the received image,
- wherein the controller is further configured to:
- detect a region in the received image, the region including pixels having same brightnesses as a brightness of a part corresponding to the reaction region in the received image, and the region including a portion of the reaction region and a portion of the reference brightness information, in the received image;
- recognize a shape of the detected region;
- determine an actual brightness of the reaction region, based on the recognized shape; and
- determine the degree of the reaction corresponding to the determined actual brightness.

22. The terminal of claim 21, wherein the controller is further configured to:
- determine the brightness of the reaction region in the received image; and
- determine the reference brightness information in the received image.

23. The terminal of claim 21, wherein the controller is further configured to determine a result of the reaction, based on the degree of the reaction.

24. The terminal of claim 21, further comprising a storage configured to store the received image of the biosensor.

25. An apparatus for measuring biometric information, the apparatus comprising:
- an input interface configured to capture an image of a reagent pad on which a sample is collected, the reagent pad comprising a reaction region at which the sample reacts, and the reagent pad displaying and indicating different discrete reference brightnesses with respect to a same color; and
- a controller configured to compare a brightness of the reaction region in the captured image with the reference brightnesses in the captured image to determine a result of a reaction between the reaction region and the sample,
- wherein the controller is further configured to:
- detect a region in the captured image, the region including pixels having same brightnesses as a brightness of a part corresponding to the reaction region in the captured image, and the region including a portion of the reaction region and one of the reference brightnesses, in the captured image;
- recognize a shape of the detected region;
- determine an actual brightness of the reaction region, based on the recognized shape; and
- determine the result of the reaction corresponding to the determined actual brightness.

26. The apparatus of claim 25, further comprising a display configured to display the captured image and the result of the reaction between the reaction region and the sample.

27. A method of a terminal measuring biometric information, the method comprising:
- capturing an image of a biosensor comprising a reaction region including a reagent that reacts with a sample, and comprising reference brightness information configured to display and indicate different discrete brightnesses with respect to a same color;
- transmitting the image to a server;
- receiving the biometric information from the server, the biometric information being determined by:
- detecting a region in the transmitted image, the region including pixels having same brightnesses as a brightness of a part corresponding to the reaction region in the transmitted image, and the region including a portion of the reaction region and a portion of the reference brightness information, in the transmitted image;
- recognizing a shape of the detected region;
- determining an actual brightness of the reaction region, based on the recognized shape; and
- determining a degree of a reaction corresponding to the determined actual brightness; and
- displaying the received biometric information.

* * * * *